(12) United States Patent
Cohen et al.

(10) Patent No.: US 10,670,504 B2
(45) Date of Patent: Jun. 2, 2020

(54) FLUIDIC DEVICE

(71) Applicant: Cambridge Enterprise Limited, Cambridge (GB)

(72) Inventors: Samuel Cohen, Leeds (GB); Tuomas Knowles, Cambridgeshire (GB); Christopher Dobson, Cambridgeshire (GB); Luke Rajah, Cambridgeshire (GB); Duncan White, Cambridgeshire (GB)

(73) Assignee: Cambridge Enterprise Limited, Cambridge (GB)

(*) Notice: Subject to any disclaimer, the term of this patent is extended or adjusted under 35 U.S.C. 154(b) by 112 days.

(21) Appl. No.: 15/921,778

(22) Filed: Mar. 15, 2018

(65) Prior Publication Data

US 2018/0328831 A1    Nov. 15, 2018

Related U.S. Application Data

(63) Continuation of application No. 14/438,145, filed as application No. PCT/GB2013/052757 on Oct. 22, 2013, now Pat. No. 9,958,369.

(30) Foreign Application Priority Data

Oct. 23, 2012  (GB) .................................. 1219014.6

(51) Int. Cl.
| | |
|---|---|
| *G01N 13/00* | (2006.01) |
| *B01F 5/04* | (2006.01) |
| *B01F 5/06* | (2006.01) |
| *B01F 13/00* | (2006.01) |
| *G01N 33/487* | (2006.01) |

(52) U.S. Cl.
CPC ............. *G01N 13/00* (2013.01); *B01F 5/045* (2013.01); *B01F 5/0647* (2013.01); *B01F 13/0093* (2013.01); *G01N 33/487* (2013.01); *G01N 2013/003* (2013.01)

(58) Field of Classification Search
None
See application file for complete search history.

(56) References Cited

U.S. PATENT DOCUMENTS

| 705,565 A | 7/1902 | Dye |
| 4,360,497 A * | 11/1982 | Casperson ............... B01J 4/001 239/132.1 |
| 5,716,741 A * | 2/1998 | Reinecke .................. G03F 7/00 205/50 |
| 5,716,852 A | 2/1998 | Paul et al. |

(Continued)

FOREIGN PATENT DOCUMENTS

| CN | 1477391 A | 2/2004 |
| CN | 102279118 A | 12/2011 |

(Continued)

OTHER PUBLICATIONS

PCT/GB2013/052757, Feb. 6, 2014, International Search Report.

(Continued)

*Primary Examiner* — Paul M. West
*Assistant Examiner* — Mark A Shabman
(74) *Attorney, Agent, or Firm* — Wolf, Greenfield & Sacks, P.C.

(57) ABSTRACT

Methods for determining the lateral diffusion of one or more components are provided.

8 Claims, 9 Drawing Sheets

(56) References Cited

U.S. PATENT DOCUMENTS

| | | | |
|---|---|---|---|
| 5,957,579 A * | 9/1999 | Kopf-Sill | B01L 3/502746 138/42 |
| 5,974,867 A | 11/1999 | Forster et al. | |
| 7,837,379 B2 | 11/2010 | Fiering et al. | |
| 8,142,741 B2 * | 3/2012 | Yoshida | B01J 19/0093 366/336 |
| 9,952,222 B2 | 4/2018 | Yates et al. | |
| 9,958,369 B2 | 5/2018 | Cohen et al. | |
| 10,295,545 B2 | 5/2019 | Yates et al. | |
| 10,386,332 B2 | 8/2019 | Herling et al. | |
| 2002/0057627 A1 * | 5/2002 | Schubert | B01F 13/0066 366/336 |
| 2002/0058332 A1 * | 5/2002 | Quake | G01N 15/1459 435/288.5 |
| 2002/0175079 A1 * | 11/2002 | Christel | B01F 5/0403 204/601 |
| 2004/0008572 A1 * | 1/2004 | Stuart | B01F 5/0256 366/162.4 |
| 2005/0007872 A1 * | 1/2005 | Nagasawa | B01F 5/0453 366/178.2 |
| 2005/0041525 A1 * | 2/2005 | Pugia | B01F 5/0655 366/341 |
| 2005/0148093 A1 | 7/2005 | Chien | |
| 2006/0163385 A1 * | 7/2006 | Link | B01F 5/0682 239/424 |
| 2006/0263903 A1 | 11/2006 | Chien | |
| 2007/0012221 A1 * | 1/2007 | Maeta | C08K 5/0041 106/498 |
| 2009/0044619 A1 * | 2/2009 | Fiering | B01F 5/0641 73/202 |
| 2009/0086572 A1 * | 4/2009 | Miyoshi | B01F 5/0057 366/181.6 |
| 2009/0223413 A1 * | 9/2009 | Takahashi | B01F 13/0062 106/400 |
| 2011/0120562 A1 * | 5/2011 | Tan | B01L 3/502723 137/1 |
| 2011/0264380 A1 | 10/2011 | Cottet et al. | |
| 2012/0218857 A1 * | 8/2012 | Ocola | B01F 5/0655 366/336 |
| 2015/0285724 A1 * | 10/2015 | Cohen | B01F 5/045 73/53.01 |
| 2018/0188145 A1 | 7/2018 | Mueller et al. | |
| 2019/0201903 A1 | 7/2019 | Douglas et al. | |
| 2019/0234530 A1 | 8/2019 | Douglas et al. | |
| 2019/0247853 A1 | 8/2019 | Douglas et al. | |
| 2019/0247855 A1 | 8/2019 | Douglas et al. | |
| 2019/0331692 A1 | 10/2019 | Yates et al. | |
| 2019/0344267 A1 | 11/2019 | Knowles et al. | |

FOREIGN PATENT DOCUMENTS

| | | |
|---|---|---|
| EP | 1481723 A1 | 12/2004 |
| JP | S63-208739 A | 8/1988 |
| JP | 2007-093374 A | 4/2007 |
| JP | 2007-292773 A | 11/2007 |
| JP | 2008-292371 A | 12/2008 |
| WO | WO 99/05512 A1 | 2/1999 |
| WO | WO 2005/033672 A1 | 4/2005 |
| WO | WO 2017/141048 A1 | 8/2017 |
| WO | WO 2017/174975 A1 | 10/2017 |
| WO | WO 2018/046952 A1 | 3/2018 |

OTHER PUBLICATIONS

GB 1219014.6, Jan. 22, 2013, Search Report.
CN 201380067708.2, Sep. 6, 2016, Office Action.
CN 201380067708.2, Aug. 29, 2016, Search Report.
CN 201380067708.2, May 2, 2017, Office Action.
JP 2015-538564, Sep. 7, 2017, Office Action.
International Search Report for PCT/GB2013/052757, Completed by the European Patent Office dated Feb. 6, 2014, 4 Pages.
Search Report for Application No. GB 1219014.6, dated Jan. 22, 2013, 5 Pages.
Chinese Search Report for Chinese Application No. CN 2013800677082, Completed by the Chinese Patent Office dated Aug. 29, 2016, 1 Page.
First Chinese Office Action for Chinese Application No. CN 201380067708.2, English translation attached to original, Both completed by the Chinese Patent Office dated Sep. 6, 2016, All together 10 Pages.
Second Chinese Office Action for Chinese Application No. CN 201380067708.2, English translation attached to original, Both completed by the Chinese Patent Office dated May 2, 2017, All together 12 Pages.
Office Action for Japanese Application No. JP 2015-538564, dated Sep. 7, 2017. 5 pages.
Aquilina et al. Proc Natl Acad Sci USA Sep. 16, 2003, vol. 100, pp. 10611-10616, "Polydispersity of a mammalian chaperone: Mass spectrometry reveals the population of oligomers in aB-crystallin".
Atencia et al. Nature Sep. 29, 2005, vol. 437, pp. 648-655, "Controlled microfluidic interfaces".
Baldwin et al. Journal of Molecular Biology 2011. vol. 13, pp. 297-309, "aB-Crystallin Polydispersity Is a Consequence of Unbiased Quaternary Dynamics".
Baldwin et al. Structure Dec. 7, 2011, vol. 19, pp. 1855-1863, "The Polydispersity of aB-Crystallin Is Rationalized by an Interconverting Polyhedral Architecture".
Bell et al. Nano Letters 2011, vol. 12, pp. 512-517, "DNA Origami Nanopores".
Benson et al. Proceedings of the National Academy of Sciences of the United States of America Feb. 1975, vol. 72, pp. 619-622, "o-Phthalaldehyde: Fluorogenic Detection of Primary Amines in the Picomole Range. Comparison with Fluorescamine andNinhydrin".
Brody et al. Sensors and Actuators A: Physical 1997, vol. 58, No. 1, pp. 13-18, "Diffusion-based extraction in a microfabricated device".
Burriel et al., Two-dimensional microfluidics using circuits of wettability contrast. Langmuir. Apr. 6, 2010;26(7):4613-5.
Chakraborty et al., Effect of dispersion on the diffusion zone in two-phase laminar flows in microchannels. Analytica Chimica Acta. Jan. 13, 2012;710:88-93.
Costin et al. Journal of Chromatography A 2003, vol. 1013, No. 1, pp. 77-91, "Diffusion coefficient measurement in a microfluidic analyzer using dual-beam microscale-refractive index gradient detection Application to on-chip molecular sizedetermination".
Culbertson et al. Talanta 2002, vol. 56, No. 2, pp. 365-373, "Diffusion coefficient measurements in microfluidic devices".
Fisher et al. Amino Acids 2001, vol. 20, pp. 163-173, "A fast and sensitive method for measuring picomole levels of total free amino acids in very small amounts of biological tissues".
Hatch et al. Nature Biotechnology 2001, vol. 19, No. 5, pp. 461-465, "A rapid diffusion immunoassay in a T-sensor".
Hatch et al. Proceedings of the IEEE 2004, vol. 92, No. 1, pp. 126-139, "Diffusion-Based Analysis of Molecular Interactions in Microfluidic Devices".
Hellstrand et al. ACS Chemical Neuroscience 2010, vol. 1, pp. 13-18, "Amyloid B-Protein Aggregation Produces Highly Reproducible Kinetic Data and Occurs by a Two-Phase Process".
Herling et al. Applied Physics Letters 2013, vol. 102, pp. 184102-1-184102-4, "Integration and characterization of solid wall electrodes in microfluidic devices fabricated in a single photolithography step".
Hortschansky et al. Protein Science 2005, vol. 14, pp. 1753-1759, "The aggregation kinetics of Alzheimer's B-amyloid peptide is controlled by stochastic nucleation".
Ingebrigtsen et al. AAPS PharmSciTech 2002, vol. 3, No. 2, 7 Pages, "Determination of the Size Distribution of Liposomes by SEC Fractionation, and PCS Analysis and Enzymatic Assay of Lipid Content".
Jehle et al. Nat Struct Mol Biol 2010, vol. 17, No. 9, pp. 1037-1042, "Solid-state NMR and SAXS studies provide a structural basis for the activation of aB-crystallin oligomers".

(56) References Cited

OTHER PUBLICATIONS

Kamholz et al. Biophysical Journal 2001, vol. 80, No. 1, pp. 155-160, "Theoretical Analysis of Molecular Diffusion in Pressure-Driven Laminar Flow in Microfluidic Channels".

Kamholz et al. Biophysical Journal Apr. 2001, vol. 80, No. 4, pp. 1967-1972, "Optical Measurement of Transverse Molecular Diffusion in a Microchannel".

Laganowsky et al. Protein Science 2010, vol. 19, pp. 1031-1043, "Crystal structures of truncated alphaA and alphaB crystallins reveal structural mechanisms of polydispersity important for eye lens function".

Li et al. ACS Nano 2013, vol. 7, No. 5, pp. 4129-4134, "Single Protein Molecule Detection by Glass Nanopores".

Litzinger et al. Biochima et Biophysica Acta 1994, vol. 1190, pp. 99-107, "Effect of liposome size on the circulation time and intraorgan distribution of amphipathic poly(ethylene glycol)-containing liposomes".

McCracken et al. Journal of Pharmaceutical Sciences Jan. 1987, vol. 76, No. 1, pp. 56-59, "Sizing of a Vesicle Drug Formulation by Quasi-Elastic Light Scattering and Comparison with Electron Microscopy and Ultracentrifugation".

Mendez., Journal of Chromatography 1985, vol. 323, pp. 373-382, "Complete Automatization of Peptide Maps by Reversed-Phase Liquid Chromatography Using o-Phthalaldehyde Pre-Column Derivatization".

Moon et al. Journal of Pharmaceutical and Biomedical Analysis 1993, vol. 11, No. 10, pp. 911-920, "Size distribution of liposomes by flow field-flow fractionation".

Nozaki et al. Science Jul. 23, 1982, vol. 217, pp. 366-367 "Siza Analysis of Phospholipid Vesicle Preparations".

Perevucnik et al. Biochimica et Biophysica Acta, 1985, vol. 821, pp. 169-173, "Size analysis of biological membrane vesicles by gel filtration, dynamic light scattering and electron microscopy".

Peschek et al. Proc Natl Acad Sci USA Aug. 11, 2009, vol. 106, pp. 13272-13277, "The eye lens chaperone a-crystallin forms defined globular assemblies".

Qin et al. Nature protocols 2010, vol. 5, No. 3, pp. 491-502, "Soft lithography for micro- and nanoscale patterning."

Roth et al. Journal of Chromatography 1973, vol. 83, pp. 353-356, "Column Chromatography of Amino Acids with Fluorescence Detection".

Roth., Analytical Chemistry Jun. 1971, vol. 43, No. 7, pp. 880-882, "Fluorescence Reaction for Amino Acids".

Selser et al. Biophysical Journal 1976, vol. 16, pp. 337-356, "A Light-Scattering Characterization of Membrane Vesicles".

Sista., Journal of Chromatography 1986, vol. 359, pp. 231-240, "Sensitive Amino Acid Analysis by Reversed-Phase High-Performance Liquid Chromatography, Otimization of the o-Phthalaldehyde Method for Composition of Picomole Amounts of AcidHydrolyzates".

Walsh et al. FEBS Journal 2009, vol. 276, pp. 1266-1281, "A facile method for expression and purification of the Alzheimer's disease-associated amyloid b-peptide".

Weigl et al. Science Jan. 15, 1999, vol. 283, No. 5400, pp. 346-347, "Microfluidic Diffusion-Based Separation and Detection".

Xia et al. Annual review of materials science 1998, vol. 28, No. 1, pp. 153-184, "Soft Lithography".

Zawieja et al. Analytical Biochemistry 1984, vol. 142, pp. 182-188, "Analysis of Picogram Quantities of Protein in Subnanoliter-Size Samples".

\* cited by examiner

FLUIDIC DEVICE

CROSS-REFERENCE TO RELATED APPLICATION

This application is a continuation of U.S. patent application Ser. No. 14/438,145 filed on Apr. 23, 2015, which is the U.S. national phase of PCT Application No. PCT/GB2013/052757 filed on Oct. 22, 2013, which claims priority to GB Patent Application No. 1219014.6 filed on Oct. 23, 2012, the disclosures of which are incorporated by reference herein in their entirety.

FIELD OF THE INVENTION

The present invention relates to flow diffusion methods and flow apparatus for analysing component mixtures, such as mixtures of polypeptides.

BACKGROUND

Many systems of fundamental or technological importance exist as polydisperse mixtures of heterogeneous components. The elucidation of the characteristic properties of the individual components in such mixtures is a crucial problem in fields ranging from analytical chemistry to biophysics.

Particle size measurement in heterogeneous mixtures of particles is a common problem in fields extending from pharmaceuticals, where size measurements diagnose the solubility and purity of therapeutic agents, to paints, inks and coatings, for all of which the size of nano and microscale components has to be controlled and monitored closely to ensure desired functionality.

A field where the sizes of nanoscale components are particularly crucial and of great defining importance is that of protein association and self-assembly; the vast majority of proteins fulfil their biological function not as monomeric species but as part of larger functional complexes; if the assembly of proteins in to such complexes does not occur in the desired manner and aberrant species are formed, this abnormal assembly frequently leads to malfunction and disease. Current biophysical techniques commonly adopted to measure the size of polypeptides perform best for homogeneous preparations of purified components, whereas the quantitative study of heterogeneous mixtures characteristic of many biological systems remains challenging.

Current microfluidic diffusion based sizing techniques [1] have been primarily directed at finding the size of a single species in a homogeneous solution [5] or measuring the interaction between two discrete species, typically using fluorescently labelled species [8, 7, 3, 11, 12, 19]. Techniques which do not require fluorescent labelling of the sample have also been reported [4].

For example, Yager et al. [11] describe a T-sensor for use in the optical measurement of transverse molecular diffusion in a microchannel. The T-sensor has two input ports through which an analyte-containing fluid and a buffer fluid are provided. The two streams of fluid are brought into contact at the T-junction and are permitted to flow side by side along a detection channel. The analyte diffuses from the analyte fluid into the buffer fluid as the flows proceed along the channel. The authors use several fluorescently-labelled proteins as test analytes, and the diffusion of these proteins is detected by fluorescence microscopy at a measurement location downstream of the junction. The methods described are focussed on the analysis of monodisperse analyte solutions.

Yager et al. note that diffusion coefficient values calculated from the recorded experimental diffusion data include an error relating to an assumption in the calculations that the fluids have a fully developed velocity profile throughout the detection channel. This assumption is not correct, as the authors explain. In fact, the velocity of the fluids is observed to accelerate along the channel from a stagnation point where the fluids are first brought into contact (a zero flow region at the junction) to the fully developed velocity at a point further downstream, in order to compensate for this region of slower fluid flow, the authors describe computational methods to explain and quantify the flow development. By the authors own admission, the solutions to the computational calculations are coarse, are slow to calculate (ca. 1 day of computational time), and can only give an idea as to the magnitude of the diffusion effects in the so-called flow development region, it follows that the diffusion coefficients calculated from the recorded data do not adequately compensate for the stagnation of fluids at the T-junction.

US 2006/263903 describes the use of a plus (+) shaped microchannel network to determine the molecular weight and the diffusivity of a sample solute. Here, a single analyte fluid flow is brought into contact with a single blank fluid flow at a cross point. The flows are subsequently separated, with each flow leaving the contact zone in a separate exit channel. The amount of analyte that has diffused into the blank fluid flow in the contact zone is determined for a range of different analyte and blank fluid flow rates. The diffusivity and molecular weight of the analyte is determined by comparison of the recorded diffusion profiles with a diffusivity profile data set generated from the diffusion of standard molecules. The methods described are focussed on the analysis of monodisperse analyte solutions.

Also known in the art are alternative fluidic methods for the determination of diffusion characteristics based on the Taylor dispersion of a species in a fluid channel. For example, US 2011/264380 describes methods for determining the hydrodynamic radius of a polydisperse species. The species to be analysed is mixed with a monodisperse standard. The resulting mixture is added to a carrier fluid flowing along a capillary tube and the Taylor profile of the mixture as it exits the capillary is recorded.

As US 2011/264380 notes, Taylor dispersion methods are not suitable for use with polydisperse mixtures, as the results obtained are simply an average signal that reflects the global properties of the mixture rather than the individual contributions of each component in the mixture. US 2011/264380 partially addresses this point by using an internal standard within a polydisperse sample, which standard provides a known contribution to the average signal. For example, where a polydisperse polymer product is analysed, an internal standard which is a monomer precursor may be present. The contribution of the polydisperse species to the overall signal may then be deduced, and the mean hydrodynamic radius of the polydisperse species may be determined. Nevertheless, this method can only provide the mean hydrodynamic radius for a polydisperse mixture. Moreover, methods based around Taylor dispersion require a time resolved measurement of diffusion, which typically has a lower sensitivity compared to the steady state methods described by Yager et al. [11].

The present inventors have developed methods of analysis that take into account the problems of analysing component diffusion in flow channels.

SUMMARY OF THE INVENTION

The present invention generally provides a method for determining the diffusion coefficient of a component, including a polydisperse mixture of components. In particular, the method may be used to determine the hydrodynamic radius of one component, preferably two or more components, within a mixture. The present method is particularly suitable for analysing polymer mixtures, such as protein mixtures. Also provided is a fluidic device for use in methods of analysis.

The method and the device of the present invention may be used to determine the diffusion coefficient and the hydrodynamic radius of a component with improved accuracy over existing methods. In some aspects, the method and the device of the present invention address the issue of fluid stagnation in a microchannel and minimise the flow development region that extends from the stagnation point, thereby allowing a stable flow to form in a reduced time.

The method of the invention allows the diffusion of one or more components to be measured over time, in this way, the method may be used to study changes in the composition of the fluids, and more particularly to study the interaction of a component with another identical component or with a different component. For example, the present invention may be used to monitor the aggregation of components in the fluids, such as the aggregation of polypeptides. Changes in the diffusive profiles of a mixture over time can be used to follow the generation and separation of aggregates of components.

A further general advantage of using diffusion methods is the opportunity to study biological molecules, such as proteins, in their native state.

In a first aspect of the invention there is provided a method for determining the diffusion coefficient of one or more components, the method comprising the steps of:
  (i) providing a component fluid flow comprising one or more components;
  (ii) providing a blank fluid flow;
  (iii) bringing the flow (i) into contact with the flow (ii) in a large cross section channel, thereby to generate two laminar flows;
  (iv) permitting the laminar flows generated in (iii) to flow from the large cross section channel info a small cross section channel;
  (v) measuring the lateral diffusion of the one or more components from the component flow into the blank fluid flow in the small cross section channel.

In one embodiment, step (i) in the method provides a component fluid flow comprising two or more components.

In one embodiment, the component fluid flow and the blank fluid flow are aqueous flows.

In one embodiment, two blank flows are provided in step (ii), and the blank flows are provided either side of the component flow in the large cross-section channel, thereby to generate three laminar flows in the large cross section channel in step (iii).

In a second aspect of the invention there is provided a fluidic device for use in the method of the first aspect of the invention, the device comprising a large cross section channel in fluid communication with two upstream supply channels, and a downstream small cross section channel in fluid communication with the large cross section channel.

The supply channels may be provided for a component fluid flow and a blank fluid flow in the method of the first aspect of the invention. The fluidic device is adapted for use with an analytical device for the detection of one or more components in the fluid flows. The analytical device is for use in measuring the diffusion of one or more components in a small cross section channel.

Where more than one component is present in a fluid, the methods described herein allow the diffusion coefficient of each component to be determined, rather than an average diffusion coefficient for the mixture of components. The deconvolution of recorded diffusion profiles may be achieved by recording a plurality of diffusion profiles at different diffusion times, which has the benefit of reducing the noise levels in the recorded data.

In a third aspect of the invention there is provided a method for determining the diffusion coefficient of one or more components, the method comprising the steps of:
  (i) providing a component fluid flow comprising one or more components;
  (ii) providing a blank fluid flow;
  (iii) bringing the flow (i) into contact with the flow (ii) in a channel, thereby to generate two laminar flows;
  (iv) measuring the lateral diffusion of the one or more components from the component flow into the blank fluid flow at a plurality of diffusion times, for example at three or more diffusion times.

The reference to a plurality of diffusion times is a reference to lateral diffusion measurements recorded at different positions along the flow channel. Thus, a second measurement point may be located downstream in the channel of a first measurement point. Further measurement points may be located at positions further downstream in the channel.

In one embodiment, step (i) in the method provides a component fluid flow comprising two or more components. Thus, step (iv) comprises measuring the lateral diffusion of two or more components from the component flow into the blank fluid flow at a plurality of diffusion times.

In one embodiment, the component fluid flow and the blank fluid flow are aqueous flows, in one embodiment, two blank flows are provided in step (ii), and the blank flows are provided either side of the component flow in the large cross-section channel, thereby to generate three laminar flows in the large cross section channel in step (iii).

In one embodiment, the method further comprises the step (v) wherein a diffusion coefficient value for a component is determined from the lateral diffusion measurements of step (iv), and optionally a hydrodynamic radius is determined from a diffusion coefficient value.

In one embodiment, step (v) includes comparing the measured lateral diffusion profiles of the one or more components from step (iv) with a series of distributions for components having known hydrodynamic radii, thereby to determine the hydrodynamic radii for each of the one or more components.

In one embodiment, step (v) comprises deconvoluting the measured lateral diffusion profiles of the one or more components from step (iv) using a highest entropy regularisation approach with reference to a series of distributions for components having known hydrodynamic radii, thereby to determine the hydrodynamic radii for each of the one or more components. In this embodiment, a least squares analysis may be used. The series of distributions for components having known hydrodynamic radii may be a series of predicted distributions.

In a further aspect of the invention there is provided a method of determining the composition of a fluid comprising a plurality of components, the method comprising the steps of:
  (i) providing one or more measured diffusion profiles for the fluid comprising the plurality of components;

(ii) providing a series of predicted distributions for components having known hydrodynamic radii; and
(iii) deconvoluting the measured lateral diffusion profiles of the one or more components using a highest entropy regularisation approach with reference to the series of distributions for components having known hydrodynamic radii, thereby to determine the hydrodynamic radii for each of the one or more components.

In one embodiment, the method of determining the composition of a fluid provides a composition profile based on the hydrodynamic radii of each component in the fluid.

The measured diffusion profiles in step (i) may be obtained or obtainable by a method according to the first or the third aspects of the invention.

In a further aspect of the invention there is provided a method for analysing a change in the composition of a fluid comprising one or more components, the method comprising the step of taking a first sample at a first time from the fluid and performing an analysis according to the first or third aspects of the invention, thereby to determine the composition of the fluid at the first time; and taking a second sample from the fluid at a second time after the first time, and performing an analysis according to the first or third aspects of the invention, thereby to determine the composition of the fluid at the second time.

The method may include taking additional, such as third and fourth, samples as later times, and performing an analysis according to the first or third aspects.

The method allows the generation of aggregates of components to be detected and the separation of components to be detected. Rates of reaction may be determined from the results.

Other aspects of the invention, and various embodiment of the invention, are as described herein.

Measurements of the steady state distribution of a sample were 10 s in duration. The total flow rate at the outlet was 40 μLh$^{-1}$.

Figure 7:
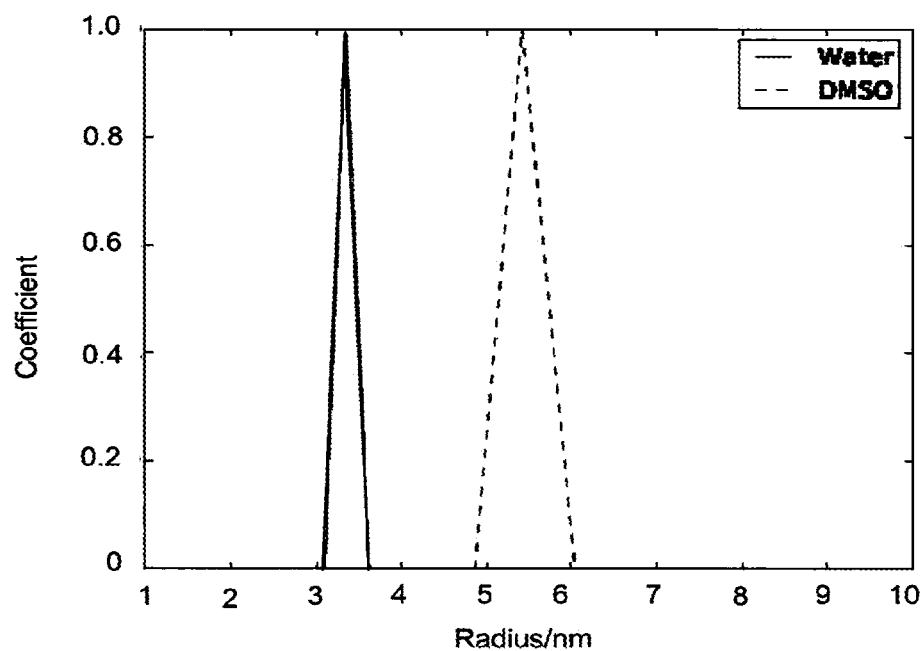

FIG. 7 shows the hydrodynamic radius of BSA in solution in pH 7 buffer and in 80% DMSO, as determined from a method of the present invention.

Figure 8:
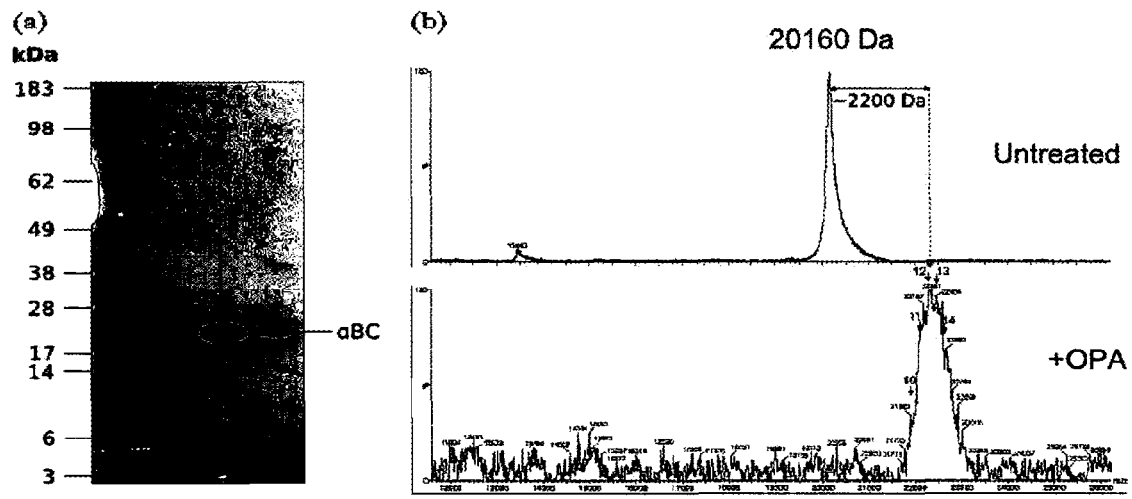

FIG. 8 shows (a) SDS-PAGE analysis of purified alpha B-crystallin. The band corresponding to approximately 20 kDa occurring under denaturing conditions is consistent with the expected molecular mass of 20,159 Da for purely monomeric alpha B-crystallin; and (b) MALDI-MS analysis of untreated and OPA-labelled alpha B-crystallin, The m/z-shift occurring upon OPA-labelling corresponds to roughly 2,200 Da. Given an increase in mass of 176 Da per label-modification, the results confirm the complete labelling of 11 amines (10 primary amines and N-terminal amine) per alpha B-crystallin molecule.

Figure 9:
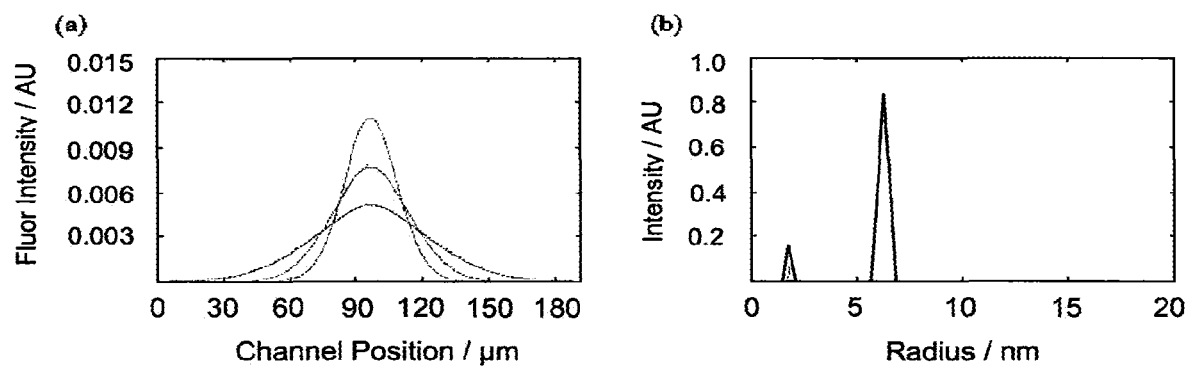

FIG. 9 shows (a) the diffusion profiles of 30 μM alpha B-crystallin in a fluidic apparatus of the invention. The experimental data (solid line) and the associated fit (dashed line) of the fluorescence intensity versus the channel position is depicted for the diffusion data at three measurement points, at 1, 3 and 9 cm, where the profiles from top to bottom at the 90 μm channel position correspond to the 1, 3 and 9 cm profile measurements; and (b) the size distribution of 30 μM alpha B-crystallin. The two populations represent monomeric and oligomeric alpha B-crystallin.

Figure 10:
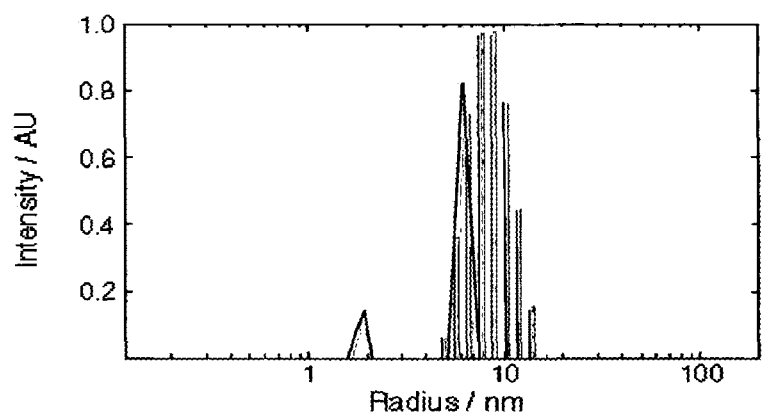

FIG. 10 shows the size distribution of 30 μM alpha B-crystallin measured with DLS (dark lines) and a microfluidic device of the present case (light lines). Diffusion spectroscopy allowed the detection of a low size species (around 2 nm) as well as oligomeric species (around 6 nm). DLS exclusively revealed one broad size distribution peak reflecting oligomeric forms of alpha B-crystallin (centred at around 8 nm).

Figure 11:
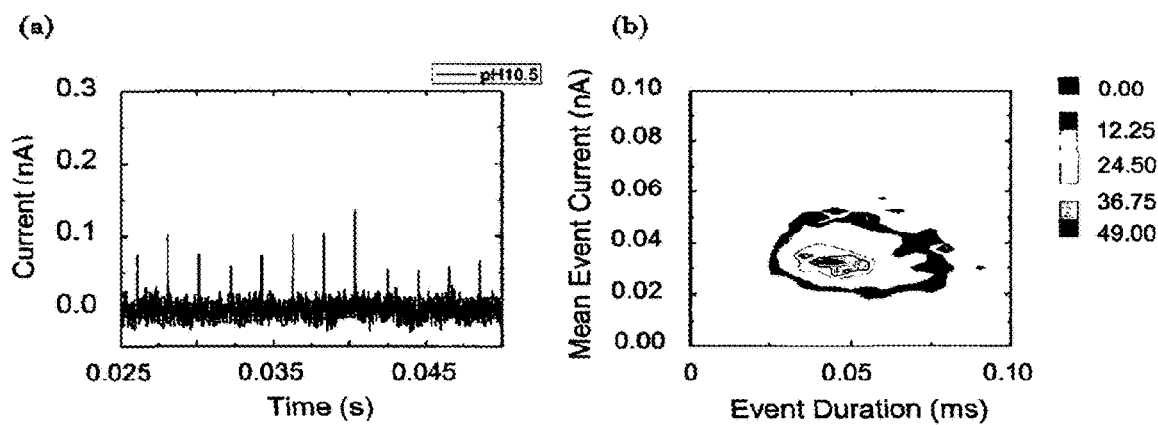

FIG. 11 shows (a) the current traces of a protein translocation experiment using alpha B-crystallin. The experiments were conducted at a negative voltage of −500 mV using a 50 kHz Bessel filter; and (b) a two dimensional scatter plot showing the relation between the mean event current and the event duration in the translocation experiment. The frequency of events is represented by the shading shown in the side scale.

Figure 12:
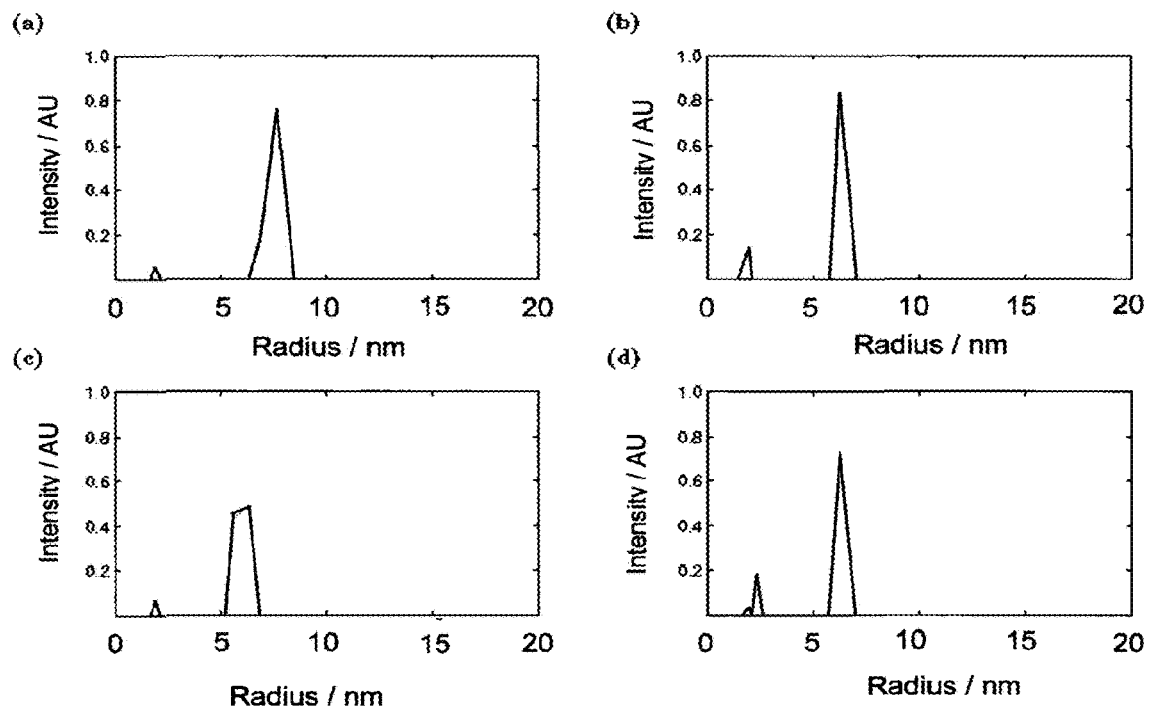

FIG. 12 shows the size distribution of alpha B-crystallin at (a) 15 µM, (b) 30 µM, (c) 50 µM, and (d) 125 µM monomeric protein concentrations, as measured by diffusion spectroscopy according to the present invention.

Figure 13:
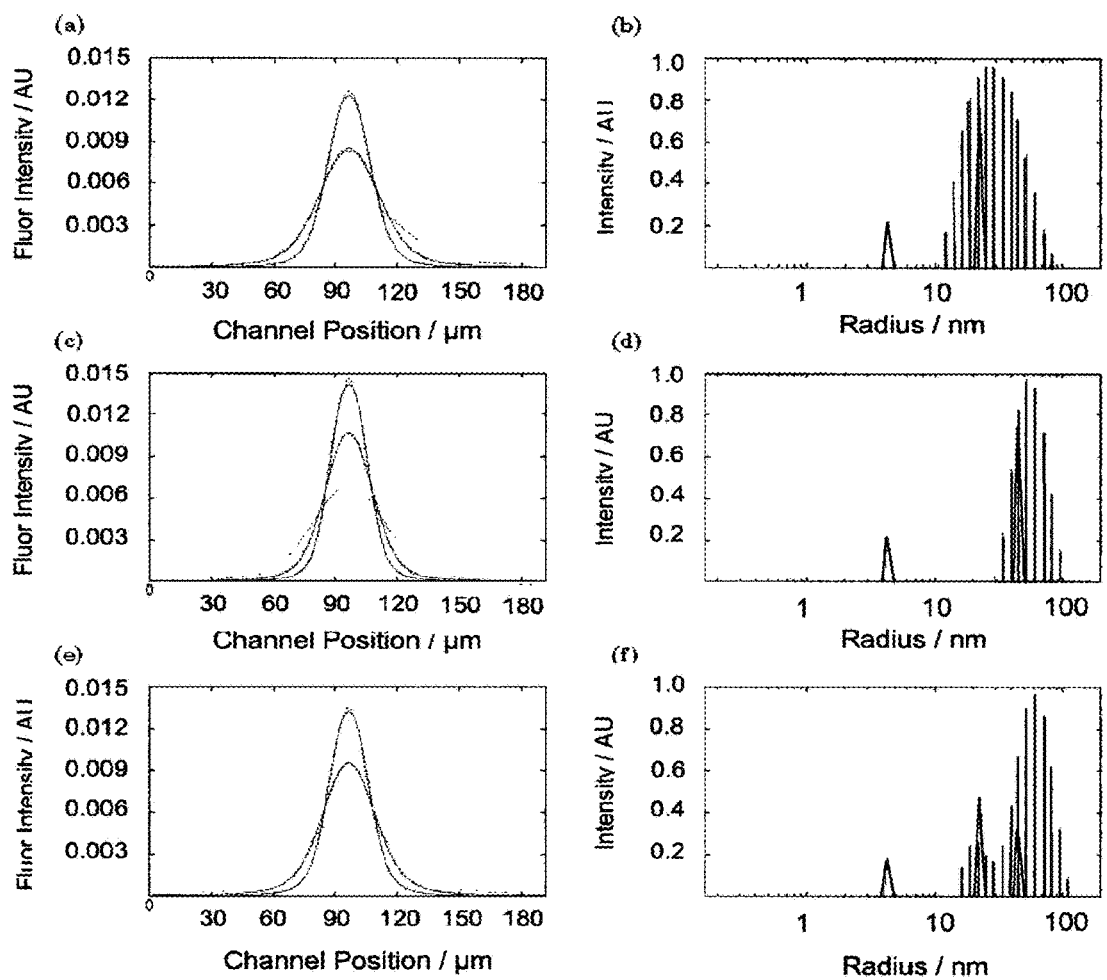

FIG. 13 shows the size distribution of liposomes as measured by diffusion spectroscopy according to the present invention, where the liposomes have (a) 15 nm and (c) 50 nm extrusion-radii and (e) a 1:1 mixture of the two. Each profile represents diffusion at different measurement points along the diffusion channel (at 1, 3 and 9 cm, where the profiles from top to bottom at the 90 µm channel position correspond to the 1, 3 and 9 cm profile measurements). For all three measurement points the fluorescence intensity profile across the microchannel is depicted (dashed line) together with the corresponding least squares fit (solid line). Size distributions of liposomes with (b) 15 nm and (d) 50 nm extrusion radii, and (f) a 1:1 mixture of the two, as measured with DLS (dark lines) and microfluidic diffusion (light lines). The peak at approx. 4 nm corresponds to free labelled lipids. Only the diffusion spectroscopy measurements identify this species.

DETAILED DESCRIPTION OF THE INVENTION

The present invention provides a method for analysing the diffusion of a component from one fluid flow into another fluid flow. The present inventors have found that changes to a standard T-junction flow device allow the diffusion of the component to be measured with greater accuracy, in particular the inventors have found a way to minimise or eliminate the stagnation of fluids when they are brought into contact at the junction.

As described herein, the inventors have found that the use of a large cross section channel at the junction where the component and blank flows contact minimises the deleterious effects of fluid stagnation on diffusion analysis. As described below, the large cross section channel may be in the region of ten times wider, for example, than the downstream channel width where the diffusion measurements are performed. The present inventors have established that a large cross section channel provides a clean and defined component flow at the junction. Thus, the present inventors have introduced a large cross section channel into a fluidic device for the measurement of component diffusion. Downstream from the large cross section channel is a small cross section channel, which is the detection channel.

The use of a large cross section flow channel is believed to provide a number of benefits. Firstly, the region where flow is established is shortened due to the relative lower flow velocity for a given flow rate. Secondly, a smaller proportion of the component enters the zero flow region since the relative size of the junction to the small flow channel decreases. Thirdly, the net effect of diffusion relative to the channel width, w, is decreased since the velocity scales with $1/\sqrt{w}$, and therefore the diffusion distance with $\sqrt{w}$.

The result of these effects is to provide a well-defined initial configuration for the components in the component flow, as the component flow and the blank flow enter the small cross section channel. The use of a large flow channel is therefore an effective way to minimise the diffusion of particles prior to the establishment of a constant velocity profile across the channel downstream, for example in the small width channel, where diffusion measurements are undertaken.

The method of the invention includes the step of measuring the lateral diffusion of components from a component flow into a neighbouring blank flow. From these measurements it is ultimately possible to determine the diffusion coefficient of a component in the sample. Whilst it is possible to determine a diffusion coefficient for a component or a mixture of components from a single measurement, the present inventors have found that multiple diffusion measurements along a small cross section channel provide accurate diffusion coefficient values.

Where the component flow comprises two or more components, the deconvolution of a single diffusion profile is particularly challenging in view of the near degeneracy in the inverse transform with respect to combinations of diffusion coefficients, in order to achieve a resolution of the individual components the diffusive spreading of the components into the blank flow is measured at a plurality of locations, for example at three or more locations. Each measurement therefore corresponds to a different diffusion time. The use of a plurality of diffusion profiles reduces the degeneracy between basis functions. The inventors have established that the use of a plurality of measurement points provides resolved size spectra that have greater accuracy (i.e. the predicted size of components more closely matches the actual size of components in the fluid) and have greater resolution (e.g. components having closer radii can be differentiated).

The flow methods of the invention allow the spatial distribution of components to be measured simultaneously at different diffusion times. In this way, it is possible to fully resolve spectra of the distributions of the diffusion coefficients of the individual components in complex mixtures. This takes the present invention beyond previously described methods, which have provided only average diffusion coefficient values for polydisperse component mixtures.

Owing to the use of small fluidic channels, particularly microfluidic channels, very small sample volumes may be analysed. Thus, components provided in fluids of less than a microliter volume may be analysed by the methods described herein. Furthermore, fluid flow techniques can also be used to analyse very dilute samples, by appropriate increases in the measurement times.

Moreover, the diffusion spectrometry approach is largely insensitive to the nature of the solvent conditions used in the flows. Thus, it is possible to study biological molecules, such as proteins, under their native conditions. In this way the diffusion measurements can provide absolute size values for the biological component, and there is no need for the analysis to include a calibration step to convert a size measurement obtained under foreign conditions to an expected size under natural conditions.

Microdevices having channels of different sizes are known, however such devices are not adapted for use in measuring the diffusion of one or more components across a channel. The present inventors have found that the development of a laminar flow in a large cross section channel, followed by the passage of the laminar flow into a small cross section channel, provides an improved method for studying the movement of components across the laminar flow.

EP 1,481,723 describes a microdevice for use in mixing and reacting fluids. The microdevice comprises a series of fluid supply passages that are arranged in a concentric multiple cylindrical construction. Fluid flows within concentric channels of the device, and these flows are permitted to join together in a reaction flow path to form a thin layer shaped laminar flow. Downstream, the width of the reaction flow path is reduced in order to contract the flow.

EP 1,481,723 does not describe methods for measuring the movement of components between laminar flows, and it does not describe methods for determining the diffusion coefficient of those components. The arrangement of channels in the device of EP 1,481,723 is to allow for the rapid diffusion of all components from one flow to another, with the aim of achieving a homogeneous distribution of all components in a short time. This is said to be important to avoid inhomogeneous reaction pathways. Within a device for the measurement of diffusion coefficients, the rapid diffusion of all species is undesirable, as it does not allow for discrimination between multiple components of different size (i.e. different diffusion coefficients). Moreover, rapid diffusion may not allow a diffusion measurement to be taken before a component has diffused to the channel edge. The teaching of EP 1,481,723 is therefore not pertinent to the development of improved diffusion measurement systems.

Diffusion

The average mean square displacement exhibited by a particle undergoing Brownian motion is directly proportional to its diffusion coefficient D and inversely proportional to its hydrodynamic radius $r_h$, the Einstein relation which allows simple estimates of molecular sizes to be obtained from average mean square displacements. The situation is more complex when a mixture of species is present in solution, each with a different diffusion coefficient.

The shape of the resulting diffusion profile may be regarded as containing the information about the full spectrum of the hydrodynamic radii of the all species present in solution as a linear superposition. However, the inverse transform of such a profile into a sum of Gauss-Weierstrass kernels corresponding to discrete species is very sensitive to experimental noise. Consequently, this approach is not generally practical as the basis for measurements in heterogeneous mixtures.

To overcome this difficulty, the present inventors have developed an approach which allows the diffusion profile resulting from the Brownian motion of analyte components, initially localised in space (within the component fluid flow), to be measured simultaneously for multiple diffusion times as they spread across the small cross section channel into the blank fluid flow.

One aspect of the present case relates to the use of a large cross section channel, which addresses the problem of zero flow at the junction where the component flow and the blank flow first contact. An advantage of the large cross section channel is that it forces the components into a well-defined initial configuration. The accurate positioning of the components in this way ensures that the recorded diffusion data is more representative of a predicted diffusion profile.

A further aspect of the present case, which may be beneficially combined with the first aspect, is the use of multiple analytical measurement points along a diffusion channel. The measurement of diffusion at different diffusion times reduces the degeneracy between basis functions, and allows diffusion coefficients to be determined with greater accuracy and greater certainty.

In a general aspect of the method of the invention, a component is permitted to move from the component flow into the buffer flow in the small cross section channel. This may be referred to as the lateral movement of the component across a channel.

In one embodiment, a component is permitted to diffuse from the component flow, an area of high component concentration, into the buffer flow, and an area of low component concentration. Here, the movement of the component is simply diffusive transport.

In an alternative embodiment, the movement of a component from the component flow to the buffer flow is a response to an applied electric field. Thus, the diffusion may be referred to as electrophoretic diffusion of the component. The component flow within the channel is deflected as a response to the applied electric field. The degree of deflection is related to the applied field and the net charge of the component. It will be appreciated that components having different charges may be separated across the channel by their differing deflections in response to the applied field, in this embodiment, it is also advantageous to minimise the flow development region, as this minimises fluid stagnation. With knowledge of the applied field and the degree of deflection (from the electrophoretic diffusion profile), the skilled person is able to determine the electrophoretic mobility and charge of the components in the fluid.

The general use of electrophoretic diffusion techniques in a microfluidic device are described by Herling et al. [37].

The method of the invention is suitable for use with other techniques that allow the lateral movement of a component across the channel. This may be broadly referred to as diffusion. In one embodiment, diffusion refers to the diffusive transport described above.

General Methods

The method of the first aspect of the invention generally looks to determine the diffusion coefficients of one or more components, such as polymers, in a solution. A fluid flow comprising the one or more components is brought into contact with a blank fluid flow in a large cross section channel. The laminar flows are permitted to flow from the large cross section channel into a small cross section channel. The lateral diffusion of the one or more components into the blank fluid flow is measured at one or more locations along the small cross section channel. From the one or more diffusion profiles it is possible to determine the diffusion coefficient and the size and/or molecular weight of the one or more components.

The large cross section and small cross section channels are parts of a fluidic device. The fluidic device is adapted for use with a detector for the components.

The flow rate of each flow is maintained at a substantially constant level during the analysis steps. The analysis may be undertaken only when a stable flow is established in the small section channel.

The method of the third aspect of the invention generally looks to determine the diffusion coefficients of one or more components, such as polymers, in a solution. A fluid flow comprising the one or more components is brought into contact with a blank flow in a channel. The diffusion of the one or more components is measured at a plurality of locations along the channel. From the plurality of diffusion profiles it is possible to determine the diffusion coefficient and the size and/or molecular weight of the one or more components.

The channel is a part of a fluidic device. The fluidic device is adapted for use with a detector for the components at a plurality of locations in the channel. The channel is in fluid communication with supply channels for the blank flow and the component flow.

The flow rate of each flow is maintained at a substantially constant level during the analysis steps. The analysis may be undertaken only when a stable flow is established in the channel.

In other aspects of the invention, a fluidic device may be used to determine the total concentration of components in the component fluid. Here, the intensity of the recorded diffusion signal (as obtained by the methods as described herein) may be used to directly obtain a total concentration of the components. In some embodiments it may be necessary to provide additional reagents to allow accurate concentration readings to be taken. For example, where the component fluid comprises polypeptides, it may be beneficial to denature the polypeptides prior to the analytical measurement. A denaturing agent, such as DMSO, may be provided in the buffer flow for this purpose.

Another aspect looks to monitor changes (or not) to a component, such as aggregation and separation, over time by taking samples of fluid containing that component, and obtaining the diffusion profiles for each sample. Changes in the diffusion profiles over time may be indicative of aggregation or separation events.

Fluidic Device

The method of the first aspect of the present invention makes use of a fluidic device comprising a large cross section channel in fluid communication with a small cross section channel. The cross section of each of the large and small channels is typically in the micrometre range, and the fluidic device for use in the method of the first aspect of the invention may therefore be referred to as a microfluidic device.

The present invention also provides the microfluidic device as described herein.

The use of microfluidic channels to hold the component and blank flows ensures that the flows fake place at low Reynolds numbers, and consequently convection and diffusion are the only relevant mechanism of mass transport within the system. Accordingly, this allows accurate numerical calculations to be performed for each component of a given size.

The general dimensions of the channels in the device are selected to provide reasonable mobilisation rates and analysis times. The dimensions of the device may also be selected to reduce the amount of fluid required for a sufficient analysis run.

The large and small cross sections channels are those channels having suitable dimensions allowing for the generation and maintenance of a laminar flow of two (or three) streams within. The laminar flow of two streams means that the flows are side by side and are stable. Thus, there are typically no regions v/here the fluids recirculate, and the turbulence is minimal. Typically such conditions are provided by small channels, such as microchannels.

Devices for use in dispersive measurements are well known in the art, and are described, for example, by Yager et al. [11]. The present inventors have introduced a large cross section channel at the junction of such devices.

The large section channel is the region where the flow of the component solution is brought into contact with the flow of the blank solution. The flows are then directed by the large cross section channel to the small cross section channel, it is in the small cross section channel that the diffusion of the one or more components into the blank flow is monitored. The large cross section channel is in fluid communication with the small cross section channel.

The large cross section channel is in fluid communication with one or more reservoirs for the supply of blank fluid.

The large cross section channel is in fluid communication with a reservoir for the supply of the component fluid.

Fluid may be provided to the large cross section channel from a reservoir by a supply channel. Thus, the device may include a component fluid flow supply channel and a blank fluid flow supply channel.

A reference to a channel herein is a reference to a channel having a substantially rectangular cross section. Thus, the channel may be formed of a substantially flat base with walls which extend substantially vertically therefrom, and optionally a top cover. Typically, the base and the walls are formed into a silicone substrate. The cover may be a glass cover, for example a standard glass slide or a borosilicate wafer.

The large section channel may be referred to as a convergent nozzle.

The large cross section channel may have a region of substantially constant maximum width followed downstream by a convergent region where the width of the channel narrows until the width matches that of the small cross section channel.

Alternatively, the large cross section channel may comprise a convergent region only, where the width of the channel narrows from a maximum width until the width matches that of the small cross section channel.

The rate at which the convergent region narrows may be constant.

The precise rate at which the convergent region narrows (the angle of the nozzle) is not particularly limited as the narrowing is usually far removed from the component flow.

However, generally the present inventors have found that nozzles having an angle in the range 40° to 70°, such as 50° to 70°, such as 55° to 65°. Here, the angle is with respect to the flow direction of the component flow in the wide cross section channel.

A reference to width is a reference to the diffusion dimension in the channel (which is referred to as d in some prior art references).

The maximum width, w, of the large cross section channel is greater than the width of the small section channel.

In one embodiment there is no section is the large cross section channel that is of a width smaller than the width of the small cross section channel, in one embodiment the minimum width of the large cross section channel is the same as the width of the small cross section channel.

The maximum width, w, of the large section channel may be at most 500 µm, at most 700 µm, at most 1,000 µm, at most 2,000 µm, at most 5,000 µm or at most 10,000 µm.

Generally channel widths of greater than 10,000 µm are not practical, as the material from which the device is made, typically PDMS, is likely to sag.

The maximum width, w, of the large section channel may be at least 50 µm, at least 100 µm, at least 200 µm, or at least 500 µm.

In one embodiment, the maximum width of the large cross section channel may be in a range selected from the upper and lower values given above. For example, the width may be in the range 200 to 5,000 µm, such as 200 to 1,000 µm, or such as 1,000 to 5,000 µm.

The length of the large section channel is at most 500 µm, at most 700 µm, or at most 1,000 µm The length of the large section channel is at least 10 µm, at least 50 µm, at least 100 µm or at least 200 µm.

In one embodiment, the length of the large cross section channel may be in a range selected from the upper and lower values given above. For example, the length may be in the range 50 to 500 μm, such as 100 to 500 μm.

Where the large cross section channel comprises a region of substantially constant maximum width and a downstream region where the width converges to the width of the small cross section channel, the region of substantially constant maximum width may be at least 50%, at least 60%, at least 70%, at least 80% or at least 90% of the total length of the large cross section channel.

The small section channel has a substantially constant width throughout its length.

The width of the small section channel may be at most 500 μm, at most 700 μm, at most 1,000 μm, or at most 2,000 μm.

The width of the small section channel may be at least 5 μm, at least 10 μm, at least 50 μm, at least 100 μm or at least 200 μm.

In one embodiment, the width of the small cross section may be in a range selected from the upper and lower values given above. For example, the width may be in the range 10 to 500 μm.

In one embodiment, the maximum width of the large section channel is at least 1.2 times, at least 1.5 times, at least 2 times, at least 5 times, or at least 10 times the width of the small section channel.

In one embodiment, the maximum width of the large section channel is at most 20 times, at most 50 times, at most 100 times the width of the small section channel.

In one embodiment, the maximum width of the large cross section channel in relation to the small section channel may be in a range selected from the upper and lower values given above. For example, the maximum width of the large cross section channel may be in the range 5 to 20 times the width of the small section channel.

The length of the small section channel may be of a length suitable to allow the diffusion of the largest component in the component flow to the channel edge forming the boundary for the blank flow. Thus, by the time the fluid flows have reached the end of the small section channel, all the components present in the component flow have reached the maximal entropic configuration.

In other embodiments, the small section channel is of a sufficient length to allow detection of the largest component in the blank flow. Here it is not necessary for the largest component to have reached its maximal entropic configuration.

The length of the large section channel is the distance from the point at which the blank and component fluid flows come into contact to the point at which the channel width of the large section channel matches that of the small section channel.

The small section channel receives the blank and component fluid flow from the large cross section channel. Fluid exiting from the small cross section channel may be collected for further analysis. Thus, the small cross section channel is in fluid communication with a sample collection reservoir.

The length of the small section channel is sufficient to allow the largest molecules to diffuse from the flow into the blank flow. For polymers having the molecular weights described herein, small section channel lengths of 1 mm length or more are generally sufficient.

In one embodiment, the small section channel is at least 0.5 mm, at least 1 mm, at least 2 mm, or at least 5 mm long.

In one embodiment, the small section channel is at most 10 mm, at most 20 mm, or at most 50 mm long.

In one embodiment, the small section channel length may be in a range selected from the upper and lower values given above. For example, the small section channel length may be in the range 0.5 to 50 mm, such as 1 to 20 mm.

The flow of the fluids is along the longitudinal axis of the small cross section channel. The diffusion of components in the component flow into the blank flow is transverse to the longitudinal axis of flow, across the width of the channel.

The small cross section channel may be substantially straight and in line with the large cross section channel. In some embodiments at least a part of the small section channel is convoluted. Thus, the small section channel may include a turn or series of turns, for example. The use of a convoluted geometry allows the size of the device to be minimised. The use of a convoluted path may also provide multiple flow channels within a single detection zone. In a single detection zone multiple channels (corresponding to different flow distances and therefore different diffusion times) may pass across a detector allowing multiple and simultaneous measurements to be made.

The small cross section channel may be in fluid communication with a fluid channel of a secondary fluidic device. The secondary fluidic device may be a device for analysing a physical or chemical property of the components in the flow.

Thus, the present invention may be used in-line with other fluidic devices to obtain characterising data for the components in the fluid flows.

The microfluidic device may be provided with supply channels providing fluid communication between the reservoir and the large cross section channel. Where two blank flows are to be provided into the large cross section channel, each of the blank flows may be delivered independently from different reservoirs. However, each of the fluid blank flows may be provided form a single reservoir that is linked to the large cross section channel via two supply channels.

Each reservoir may be a syringe which is connected to a supply line of the microfluidic device. The syringe may be under the control of a suitably programmed computer which is capable of indecently controlling the flow rate of fluid from the reservoir to the large section channel. The control of such devices is well known in the art.

Alternatively each reservoir may be provided as part of the microfluidic device.

In other embodiments, the flow of fluid from one or more reservoirs may be a gravity feed.

A fluidic device according to the present invention and for use in the methods described herein may be prepared using standard techniques known in the art. Thus, photolithography may be used to generate fluid channels and optionally fluid reservoirs, in an appropriate substrate, such as a silicone substrate. The techniques described in Yager et al. [11] may be used with appropriate adaptations to the photolithographic mask to accommodate the introduction of a large cross section channel and additional blank flow channels, where appropriate.

Fluidic channels prepared by photolithographic techniques may be finished by providing fluid access and exit ports, for example by drilling into the substrate to provide access to the relevant channels. Where external reservoirs, such as syringes, are used to supply fluids directly to the large cross section channel or to a supply channel, an appropriate manifold may be used.

The fluidic device may be used in combination with a suitably programmed and programmable computer for controlling the flows into the large cross section channel and for managing the detection device. The computer may also analyse the recorded data and provide real time diffusion values.

The device is suitable for integration with a detector for measuring the lateral diffusion of the one or more components in the small cross section channel.

The channel depth may be selected to reduce the time scale for analyte diffusion across the channel width (thereby to reduce the time taken to approach the steady state solution). The depth of the channel may be selected so as to minimise or eliminate artefacts that are associated with the deepest channels (see Yager et al. *Biophysical*). The depth of the channel may be selected so as to minimise or eliminate loading problems and high fluid resistance that are associated with very shallow channels (ibid.).

In some prior art references the height or depth of the channel is referred to as the width, w.

The aspect ratio, the ratio of the width of the channel to the height of the channel, may be 100 or less, 50 or less, 25 or less, or 10 or less.

The aspect ratio may be 1 or more, 2 or more, 4 or more, or 5 or more.

In one embodiment, the aspect ratio may be in a range selected from the upper and lower values given above. For example, the aspect ratio may be in the range 5 to 100.

Generally larger aspect ratios, such as 4 or more, are favoured as the fully developed velocity profiles will be parabolic across the channel height and approximately blunt across the channel width (see Yager et al. *Biophysical*).

The channel height (or channel depth) of the large section channel and/or the small section channel is not particularly limited, save for the considerations discussed above. The channel height of the large and small cross section channels may be the same. The channel height is substantially constant throughout the large and small cross section channels, In one embodiment, the channel height is at least 5 µm, at least 10 µm, or at least 15 µm. In one embodiment, the channel height is at most 30 µm, at most 50 µm, at most 100 µm, or at most 500 µm.

In one embodiment, the channel height may be in a range selected from the upper and lower values given above. For example, the channel height may be in the range 10 to 50 µm.

Channels known from the prior art typically have a depth in the range 10 to 100 µm (see Yager et al. [8, 11 and 12]).

As noted above, the depth of the channel may be selected in relation to the width of the channel to provide a suitable aspect ratio.

It is not necessary to separate the laminar flows from each other in order to perform the analytical analysis. The analytical measurement may be recorded across both the component flow and the blank flow.

The method of the third aspect of the present invention makes use of a fluidic device comprising a channel in fluid communication with supply channels for the blank flow and the component flow. The dimensions of the channel in this aspect of the invention may correspond to the dimensions of the small cross section channel in the methods and devices of the first and second aspects of the invention.

The device of the invention may include supply channels in fluid commination with the large cross section channel. The dimensions of each supply channel are not particularly limited and may be similar to or the same as the small cross section channel, in one embodiment. Each supply channel has a width that is greater than the width of the small cross section channel, in one embodiment, each supply channel has a width that is less than the width of the small cross section channel.

In one embodiment, the methods of the present case make use of electrophoretic diffusion to permit movement of a component across the fluid flow, for example from the component flow into the buffer flow. For example, the fluidic device may be provided with electrodes arranged adjacent to the diffusion channel (the small cross section channel) and the electrodes may be adapted for electrical communication with a power supply and controller for controlling voltage and current. Suitable apparatus for directing component movement in a fluid channel is described by Herling et al. [37].

Detection

Certain methods of the invention include the step of determining the distribution of a component or components across a fluidic channel. There are no particular restrictions on the way that the diffusion of a polymer into the blank flow is measured, and the detection method employed may be based on the nature of the component to be detected.

The detector is one that is suitable for use with fluidic flow channels, and particularly microfluidic channels. Diffusion detection methods are well known in the art and are described by Yager et al. [11], for example. Examples include UV-vis, fluorescent or luminescent spectroscopic methods, amongst others.

The distribution of the component or components may be determined at one location in the small cross-section channel. However, particularly where two or more components are present, the distribution of component may be determined at two or more, such as three, four or five, locations along the smaller cross-section channel. As noted above, the method may include the step of determining the diffusion profile of components at a plurality of locations in the small width channel.

At least one diffusion measurement should be recorded before a component in the component flow has diffused to the channel edge that is the boundary of the device to the blank fluid flow. The component that will diffuse most quickly to the channel edge is the smallest component in the component flow.

For a sample of unknown composition a trial flow may be established to determine at what point the first component reaches the boundary edge. The first diffusion measurement may therefore be taken upstream of this point.

Alternatively, a first diffusion measurement may be performed at a very early point in the small cross section channel.

Where multiple diffusion measurements are made along the small cross section channel, the location of each the second and subsequent along the channel is not particularly limited. Typically, the subsequent measurements are taken at sufficiently further distances along the small section channel to give diffusion profiles of useful difference to previous measurements.

In the methods of the present invention a laminar flow of the component flow and the blank flow is established and is provided in the small cross section channel. When the flow is established, a gradient of diffusion is provided along the small cross section channel. Data for different diffusion times may therefore be obtained simultaneously by analysing the diffusion profile at two or more locations along the small cross section channel.

The methods of the present invention do not require the separation of the blank flow from the component flow. Thus, the diffusion profile of the one or more components may be measured whilst the component flow and the bank flow are in contact.

Yager et al. [11] describe the measurement of the diffusion profile at a single measurement location in a channel having a component flow (with a single component) and a blank flow.

In the fluidic system of US 2006/263903, a blank flow is diverted from the component flow after a period of contact in a cross channel region. At the contact point, a component in the component flow may diffuse into the blank flow. The separate blank flow is analysed and the amount of component quantified. To obtain a diffusion coefficient value for the component, it is necessary to take several measurements over time at a variety of different flow rates for the blank flow, the component flow, or both.

Prior to analysis, the components of interest may be labelled to allow their detection in the method of the invention. The label may take the form of a chemical group that is detectable by standard UV-vis, fluorescent or luminescent spectroscopy, for example.

Component and Component Flow

The present invention may be used to determine the diffusion coefficient and therefore the hydrodynamic radius of a component, in a preferred embodiment of the invention, the component is or comprises a polymer.

The present invention may be used to determine the diffusion coefficient of a single component, for example in solution. However, the present invention may be used advantageously to determine the diffusion coefficients of two or more components in a fluid.

Each component may be a dissolved in the fluid. However, the present invention may also be used to study components that are dispersed within a fluid. Thus, the fluid used in the method may be colloidal, and may be a sol or an emulsion, where the component is the dispersed phase.

Aqueous fluids are typically used in the methods of the invention. The component or components may be taken into solution for the purposes of performing the method of the invention. The components may already be in solution and this solution may be used directly as the fluid. Alternatively, such a solution may be concentrated or diluted as appropriate for optimal analysis. The solution may also contain additional reagents for the purpose of stabilising the components in solution, for example for maintaining the structural integrity of the component of for retaining the components in solution. For example, the components may be provided in a buffered solution.

The aqueous fluid flow may be at a pH suitable for maintaining the integrity of the components within the flow. The pH may be in a range from pH 4 to 10, such as 5 to 9, such as 6 to 8.

The pH may be physiological pH.

Alternatively, the pH of the aqueous mixture may be chosen so as to bring about changes in the composition of the mixture, such as aggregation and separation events, which may be monitored using the methods of the invention.

An aqueous fluid flow may additionally comprise a miscible organic solvent. This may be provided to retain components in solution or suspension. For example, DMSO may be used together with water. The organic solvent may be present at up to 25%, up to 20%, up to 10%, up to 5% or up to 1% v/v.

The amount of component required to perform an analysis according to the method of the invention is not large, and very small quantities of material may be passed through the microfluidic device. It is also possible to collect the fluid exiting the small section channel, and this may be reanalysed, for example after appropriate concentration of the collected fluid flow.

A reference to a component mixture is a reference to a solution of two or more components having different molecular weights and/or different diffusivities. The component mixture may have three, four, five or more components each having different molecular weights and/or different diffusivities.

A reference to a component may be a reference to a polymer.

A polymer may be or comprise a polypeptide.

References to polypeptides include references to proteins, antibodies.

A polymer may be or comprise a polysaccharide.

A polymer may be or comprise a polynucleotide.

In one embodiment, a component may comprise a polymer bound to another compound. The other component may be a component as described herein. In one embodiment, a component may comprise two or more polymers which are held in aggregation. For example, the component may comprise two or more polypeptides. As described herein, the present methods may be used to detect the formation of aggregates, such as polypeptide aggregates.

Where a component comprises two or more polymers, the polymers may be held together by covalent bonding or non-covalent bonding, or a combination thereof. Examples of covalent bonding between polymers may include ester, amide and disulphide linkages. Examples of non-covalent binding include hydrogen bonding, ionic bonding, and $\pi$-$\pi$ interactions, amongst others.

In one embodiment, the component is a nanoparticle, for example a particle having a largest dimension in the range 1 to 500 nm, such as 5 to 100 nm. The particle may be a metal nanoparticle. The metal may be or include gold or silver.

The present invention is suitable for determining the diffusivity of polymer molecules having a molecular weight of 300 Da or more, 500 Da or more, 1,000 Da (1 kDa) or more, or 2 kDa or more.

The present invention is suitable for determining the diffusivity of polymer molecules having a molecular weight of 5 kDa or less, 10 kDa or less, 50 kDa less, or 100 kDa or less.

The present invention is suitable for determining the diffusion coefficients of polymers molecules having radii of at least 0.05 nm, at least 0.1 nm, at least 0.5 nm, at least 1 nm, or at least 5 nm.

The present invention is suitable for determining the diffusion coefficients of polymers molecules having radii of at most 10 nm, at most 15 nm, at most 25 nm, at most 50 nm, at most 100 nm, or at most 200 nm, or at most 500 nm.

In particular, the present invention is particularly suitable for determining the diffusion coefficients of biopolymers, such as polypeptides which have radii in the range 0.5 to 500 nm, such as 0.5 to 200 nm, such as 0.5 to 15 nm.

The method of the invention includes the step of measuring the diffusion of components into the blank flow. The components may be detectable using standard analytical techniques such as fluorescent spectroscopy, luminescent spectroscopy, UV-vis spectroscopy amongst others. Where the component is a polypeptide, for example, the polypeptide may be detected by fluorescent spectroscopy.

In some embodiments it may be necessary to label a component to allow it to be detected in the small section channel. The label is an analytically detectable atom or group. In one embodiment, the label may be a UV-vis, fluorescent or luminescent label that is covalently attached to the component. Such labels are commonly used with biological molecule such as polypeptides, polynucleotides and polysaccharides. An example of a label for use in the present invention is fluorescein. The labels for use in the present invention are typically relatively small compared to the component to which it is attached. Thus, the label does not substantially alter the diffusion properties of the component.

Where appropriate, a component may have a plurality of labels, to assist detection.

A reference to a component may be regarded as a reference to a component having an analytical label.

An advantage of the present invention is that each component in a component fluid may be identically labelled. The methods of the invention are capable of distinguishing and identifying components based on the diffusion profile of the component. It is not necessary to label the components of interest using separate and distinct labels.

The flow rate of the component flow may be altered independently of the flow rate of the blank flow.

The component flow may be generated from an analyte sample containing one or more components. The analyte sample may be diluted or concentrated as appropriate to provide a component fluid that is suitable to flow through a device as described herein, and is suitable for detection.

The concentrations of the components in the fluid may be selected so as to ensure that the components themselves do not have an effect on the viscosity of the fluid. The concentrations of the components in the fluid may be selected so as to ensure that the components are easily detectable within the fluid flow.

In principle the maximum concentration for use in the methods may be the concentration at which the fluid is saturated with the components.

The inventors have found that fluids having a concentration of a component as low as 0.1 μM, for example as low as 0.5 μM, including as low as 1 μM, may be used in the methods of the invention. At these concentrations, it is possible to obtain meaningful distribution profiles. At lower concentrations the components may be difficult to detect in the small cross section channel, and the signal to noise ratio may be poor.

Of course, the precise composition of the analyte sample may not be known, and the generation of the fluid may be based on an initial series of test runs to establish the conditions of use. The preparation of the fluid may also be based on preliminary analysis of the sample to provide at least a rough indication of concentration.

Blank Fluid and Blank Fluid Flow

The method of the invention includes the step of monitoring the diffusion of one or more components from a component flow into a blank flow.

In one embodiment, the blank fluid may be the same as the component flow without the components.

In one embodiment, the blank fluid is a buffer.

Typically, the blank fluid flow and the component flow are aqueous flows.

The one embodiment, the blank fluid may comprise additional reagents, where such reagents are for interaction with one or more components in the component fluid, in some embodiments of the invention, there is provided a binding assay for determining an analyte concentration. Here, for example, the interaction of a known concentration of a reagent in the blank flow with a partner from the component flow allows the concentration of the component to be determined from the fraction of component bound to reagent. Such methods are particularly suitable for use where the reagent is an antibody and the component is an antigen.

The flow rate of the blank flow may be altered independently of the flow rate of the component flow.

In some embodiments, two blank flows are provided on either side of the component flow. The method of the invention may therefore look at the diffusion of components in the component into either or both of the blank flows. The use of two blank flows is advantageous as these may be used to provide a stable balancing pressure across the component flow.

Typically, the composition of the two blank flows is identical. Typically the flow rate of the two blank flows is identical.

Analysis and Determination of Diffusion Coefficient

The present invention provides methods for determining the diffusion coefficient of a component or components in a fluid.

Where the component fluid contains a monodisperse component, it is possible to determine the hydrophobic radius of the component using standard techniques. Such are described, for example, by Yager et al. [8, 11 and 12], The diffusion profile recorded in the method of the first aspect of the invention may be regarded as more representative of the diffusion of the component in view of the fact that the large cross section channel limits the effects of stagnation at the junction of the device.

Accordingly, the calculated diffusion coefficient value, and the hydrophobic radius, may be considered as having greater accuracy.

Where the component fluid contains a polydisperse mixture of components, the present invention provides a method for determining the diffusion coefficients of two or more, or each component in the mixture. This is in contrast to methods known in the art which typically provide only an average diffusion value for the global mixture, in the method of the third aspect of the invention a plurality of diffusion measurements are recorded over different diffusion times.

As noted herein, the methods of the invention provide two laminar fluid flows. The methods are conducted at low Reynolds numbers where convection and diffusion are the only relevant mechanisms of mass transport. This simplifies the simulation of component movement within a channel.

Generally, the recorded diffusion spectra are deconvoluted with respect to a series of theoretical diffusion profiles determined for a range of components having hydrodynamic radii (and therefore diffusion coefficients) across the likely range of radii for the components under investigation. The deconvolution step fits the recorded data to the global profile made up from the most likely collection of individual theoretical diffusion profiles. The fit is made for the simplest solution consistent with experimental error. In context, the reference to the simplest solution is a reference to a highest entropy regularisation.

The deconvolution of recorded diffusion profiles is made in reference to a generated basis function. The basis function is a collection of theoretical diffusion profiles where each theoretical profile is for a component having a particular hydrodynamic radius. The collection is made up of profiles for a range of hydrodynamic radii. For samples containing polypeptides, for example, the profiles span the range of likely radii for polypeptide components, such as 0.5 to 200 nm such as 0.5 to 15 nm.

A repression analysis of the recorded data, using a least-squares fit, is undertaken with maximum entropy regularisation. In combination with the simulated basis function, the recorded spatial profiles may be deconvoluted into a spectrum of individual diffusion profiles.

The deconvolution methods described above are advantageous for they provide the solution within error of the best fit containing the least information. This in turn prevents so-called over-fitting of the data.

In further detail, the present methods allow accurate numerical calculations to determine kernels for species of given sizes. The diffusion profiles acquired in the flow experiment are then fitted globally to a linear superposition of the predicted kernels, where the amplitudes of each kernel are determined through a constrained least squares fitting where the coefficients are restricted to the interval 0 to 1 to ensure their physical interpretation as fractional concentrations. The residuals in the fit provide an estimate of the error in the measurement. A second series of least-squares fits is then performed, this time with maximum entropy regularisation. The entropic term is gradually increased in magnitude until the $\chi^2$ value for the regularised fit is different to that of the unregularised fit by the random error level. The coefficients for this final fit are then the simplest (highest entropy) solution consistent with the experimental error.

Figure 5:
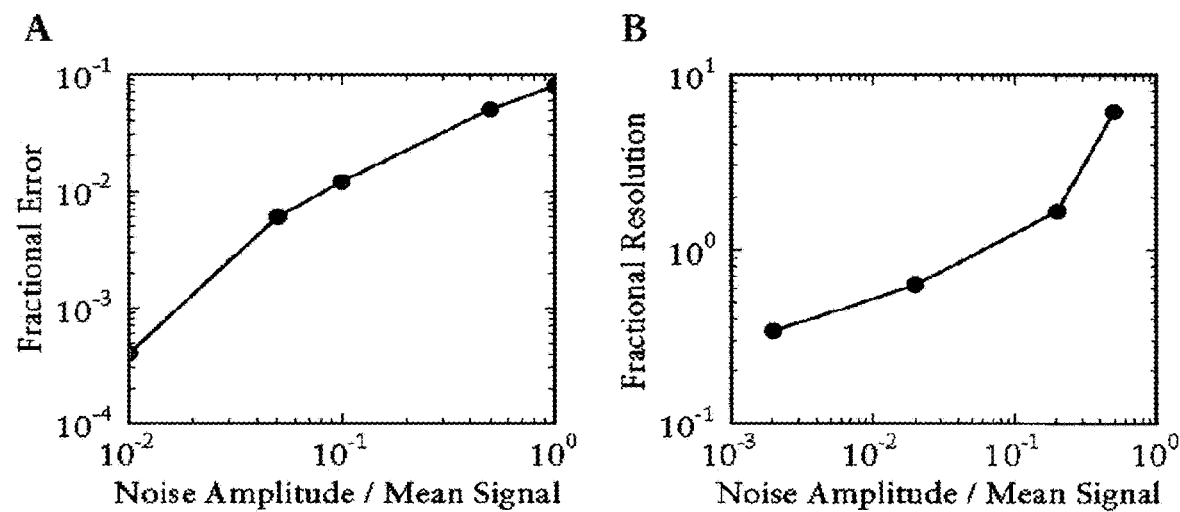
FIG. 5 shows the numerical estimate of the resolution of microfluidic diffusion spectrometry where (A) is the fractional error in the position of a single peak when resolving a single species with varying levels of random noise, and (B) is the minimum fractional difference between two species before they are resolved at varying levels of random noise.

Whilst the least squares fit provides an estimate of the noise level in the experimental data, it is useful to have an estimate of the overall precision of the technique. Here this is obtained by generating a large dataset of artificial data with varying levels of random noise added. FIG. 5 describes the two most relevant measures of precision—the precision in determining the diffusion coefficient of a single species, and the minimum resolvable difference in diffusion coefficient between two discrete species—for differing levels of random noise. This method neglects any systematic errors introduced, for example during device fabrication, or by uneven illumination of the sample.

The hydrodynamic radius of a component may be determined from the diffusion coefficient, as known in the art.

The diffusion profiles may also be used to determine the concentration of components in the component fluid, as known in the art.

Methods of the Invention

In one aspect, the present invention provides a method for determining the diffusion coefficient of a component or each component in a mixture of components. The method comprises the steps of:
  (i) providing a component fluid flow comprising one or more components;
  (ii) providing a blank fluid flow;
  (iii) bringing the flow (i) into contact with the flow (ii) in a large cross-section channel, thereby to generate two laminar flows;
  (iv) permitting the laminar flows generated in (iii) to flow from the large cross-section channel into a small cross-section channel;
  (v) measuring the lateral diffusion of the one or more components from the component flow into the blank fluid flow in the small cross-section channel.

The methods of the invention are typically performed in flows having a low Reynolds number. For example, the Reynolds number of a flow may be 1 or less, 0.5 or less, 0.1 or less, or 0.05 or less.

In one embodiment the fluid flow rate is at least 1, at least 5, at least 10, at least 50, or at least 100 $\mu L h^{-1}$.

In one embodiment the fluid flow rate is at most 200, at most 400, at most 500, at most 1,000, at most 2,000 or at most 5,000 $\mu L h^{-1}$.

In one embodiment, the flow rate is a value selected from a range having upper and lower values selected from the values above. For example, the flow rate may be in range 5 to 400 $\mu L h^{-1}$.

The fluid flow rate is the flow rate at steady state.

The use of microfluidic devices with flow rates in the range indicated above means that relatively small quantities of component fluid may be used in an analytical run. For example, volumes in the range are sufficient to establish a steady state flow in the small cross section channel for the purposes of obtaining at least one diffusion profile reading.

In one embodiment, the total volume of fluid used in the component fluid flow is at most 50, at most 100, at most 200, at most 500, or at most 1,000 $\mu L$.

In one embodiment, the total volume of fluid used in the component fluid flow is at least 0.1, is at least 0.5, is at least 1, is at least 5, or is at least 10 $\mu L$.

In one embodiment, the total volume of fluid used in the component fluid flow is a value selected from a range having upper and lower values selected from the values above. For example, the total volume may be in range 1 to 50 $\mu L$.

The methods of the invention may be performed at or around room temperature, for example 15, 20 or 25° C. Alternatively, the methods of the invention may be conducted at lower temperatures, such as 5 or 10° C., or higher temperatures, such as 35, 40 or 50° C.

In one embodiment, the lateral diffusion of the one or more components from the component flow into the blank fluid flow is measured at a plurality of diffusion times. The separation between measurement points is not particularly limited, but may be of sufficient distance that the recorded diffusion profiles have noticeably changed between measurement points.

In one embodiment, the method comprises repeating steps (i) to (v) after a period of time, thereby to analyse the composition of a component fluid over time. In this embodiment, the method may be used to monitor a change in the component fluid, such as the aggregation of the components, or the separation of a component, which may be an aggregation, into smaller parts. Described herein is a method for analysing the aggregation of amyloid proteins.

In one embodiment, the method further comprises the step (vi) wherein a diffusion coefficient value for a component is determined from the lateral diffusion measurements of step (v). and optionally a hydrodynamic radius is determined from a diffusion coefficient value.

In one embodiment, step (vi) includes comparing the measured lateral diffusion profiles of the one or more components from step (v) with a series of distributions for components having known hydrodynamic radii, thereby to determine the hydrodynamic radii for each of the one or more components.

In one embodiment, step (vi) comprises deconvoluting the measured lateral diffusion profiles of the one or more components from step (v) using a highest entropy regularisation approach with reference to a series of distributions for components having known hydrodynamic radii, thereby to determine the hydrodynamic radii for each of the one or more components, in this embodiment, a least squares analysis may be used. The series of distributions for components having known hydrodynamic radii may be a series of predicted distributions.

In an alternative method of the invention, there is provided a method for determining the diffusion coefficient of one or more components, the method comprising the steps of:

(i) providing a component fluid flow comprising one or more components;
(ii) providing a blank fluid flow;
(iii) bringing the flow (i) into contact with the flow (ii) in a channel, thereby to generate two laminar flows;
(iv) measuring the lateral diffusion of the one or more components from the component flow into the blank fluid flow at a plurality of diffusion times.

The separation between measurement points is not particularly limited, but may be of sufficient distance that the recorded diffusion profiles have noticeably changed between measurement points.

The flow rates, volumes and temperatures discussed above are applicable to this method also.

In one embodiment, the features of the first and third aspects of the invention may be advantageously combined to provide a method for analysing a component fluid with improved accuracy. The method may therefore comprise the steps of:
(i) providing a component fluid flow comprising one or more components;
(ii) providing a blank fluid flow;
(iii) bringing the flow (i) into contact with the flow (ii) in a large cross-section channel, thereby to generate two laminar flows;
(iv) permitting the laminar flows generated in (iii) to flow from the large cross-section channel into a small cross-section channel:
(v) measuring the lateral diffusion of the one or more components from the component flow info the blank fluid flow at a plurality of diffusion times.

The advantages of using a large cross section channel and the advantages of recording a plurality of diffusion profiles may therefore be brought together.

OTHER PREFERENCES

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXPERIMENTAL

Figure 1A:
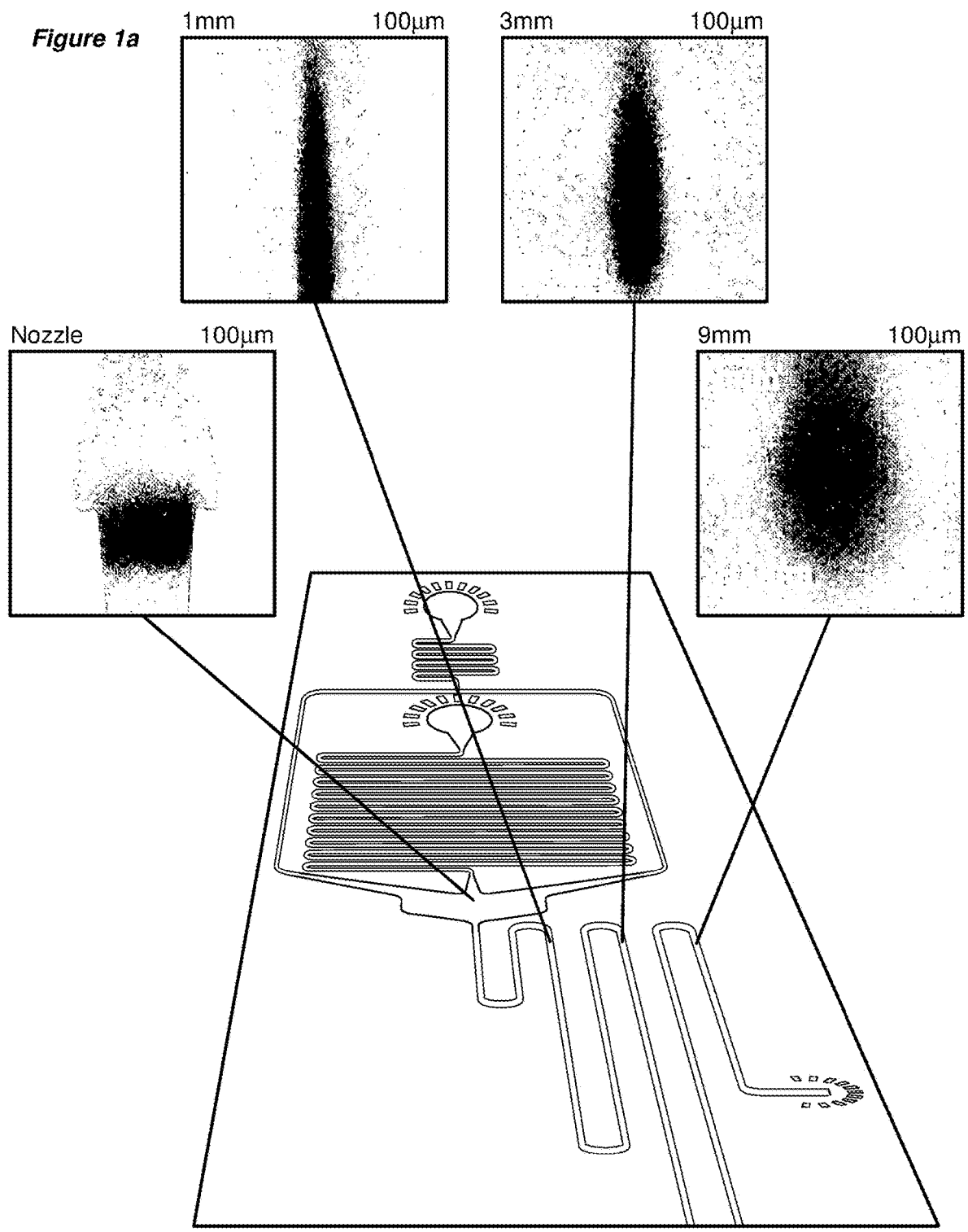
FIG. 1a is an illustration of a part of a fluidic device according to one embodiment of the invention in use, with images showing the distribution of a component fluid flow (in this case a mixture of Bovine Serum Albumin and Beta Lactoglobulin in water) at the nozzle, and the three measurement regions at 1 mm, 3 mm and 9 mm along the measurement channel (the small cross section channel). Blank flows (white) are provided either side of the component flow (black).
Figure 1B:
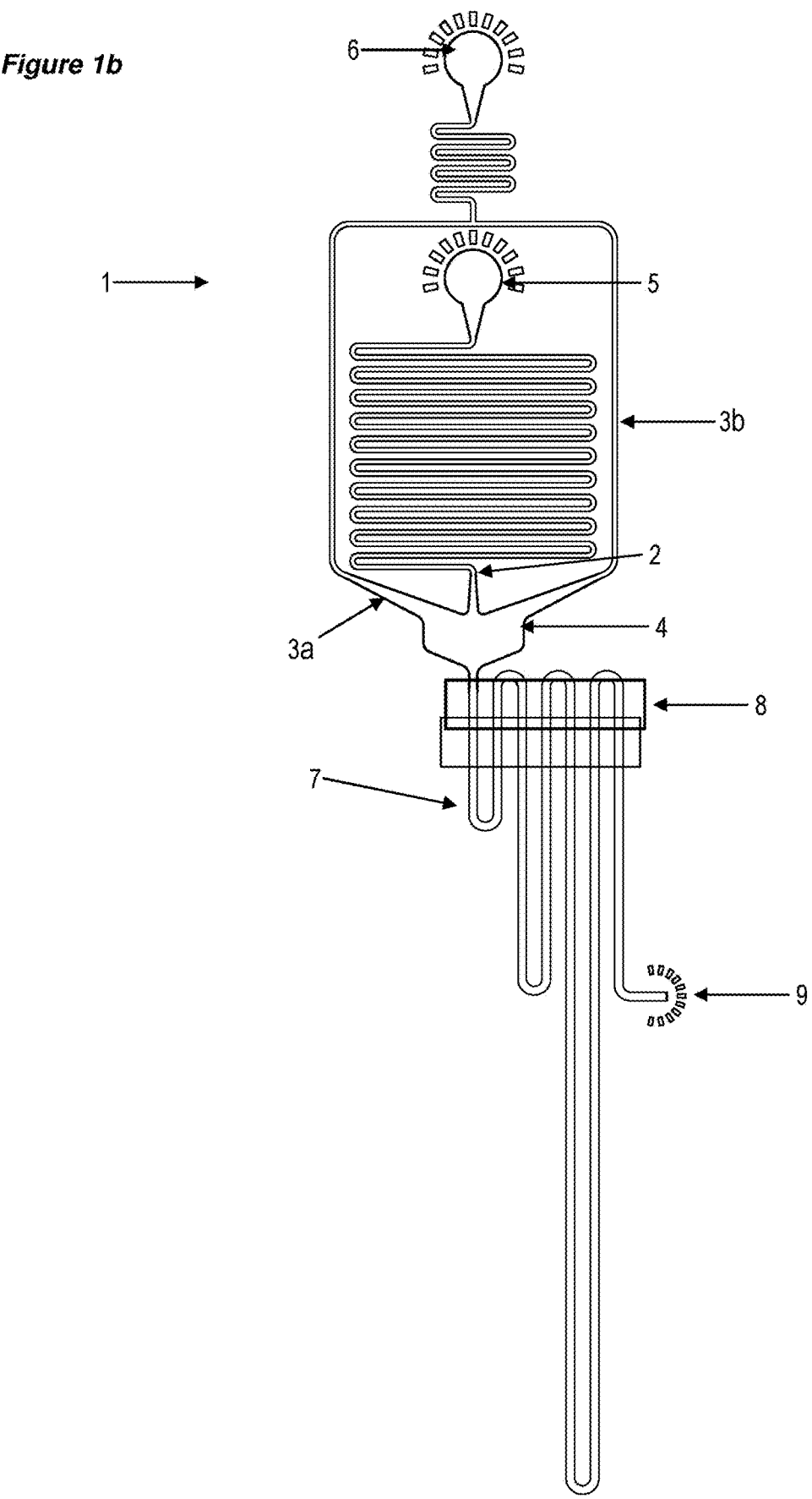
FIG. 1b is a plan drawing of the illustration of FIG. 1b.

Microfluidic channels were fabricated using standard soft-lithography techniques [20, 14] into polydimethylsiloxane (PDMS; Dow Corning) with SU-8 photoresist on silicon masters. The channels were plasma bonded to glass slides to create sealed devices. The channel height was 25 μm. Channel width varied across different regions of the device—in the small cross section channel the width was 300 μm, contracting from 3,000 μm at the nozzle (the large cross section channel). Channels introducing buffer (blank) fluid and analyte fluid into the nozzle were 100 μm in width. The device used in the experiments described herein is shown in FIGS. 1a and 1b. Further preparation details are also described below.

Syringe pumps (Harvard Apparatus) were used to control fluid flow.

The 25 nm and 100 nm colloids used in the present case were polystyrene colloids from Sigma Aldrich that were supplied pre-labelled with fluorescein. The colloids were provided in deionised water. The flow rate used was typically 4 μL/h.

The proteins for use in the present case were Glucagon, beta-lactoglobulin, and bovine serum albumin, all available from Sigma Aldrich, The proteins were fluorescently labelled. The proteins were provided in 50 mM Phosphate buffer with 20% DMSO at pH 8. The flow rate used in the protein experiments was typically 40 μL/h.

Diffusion of the components in the channel was measured by fluorescent detection across the channel using standard techniques (see also Yager et al. [11] et al.). The exposure time was typically 10 s.

Aβ(1-42) was cloned into the "PetSacKan" plasmid, recombinantly expressed in *E. Coli* BL21 cells, and purified in batch mode using anion exchange chromatography. This procedure allows for the production of large quantities of highly pure peptide [18]. The resulting peptide was divided into 1 mL aliquots, lyophilized, and stored at −20° C. until further use.

The application of diffusion spectrometry to the study of complex protein association processes like those described here relies on our use of a non-perturbative covalent labelling technique recently reported in detail. Given that the main advantage of diffusion spectrometry is its ability to obtain the spectrum of particle sizes in a heterogeneous mixture, in deciding on a labelling technique to allow the visualization of the diffusive flow under observation, fluorescent covalent labelling is the optimal method. Fluorescent labelling facilitates the convenient collection of high signal-to-noise images with a routine optical microscopy setup. Covalent labelling ensures that all species within the heterogeneous mixture are labelled and thus able to be detected. Historically, covalent fluorescent labelling of protein complexes has been challenging. If preformed protein complexes are labelled with a fluorescent dye, the unbound dye must be removed from the reaction mixture prior to the analysis, and the required purification steps disrupt the structure of the associated species transiently formed.

Alternatively, individual proteins may be labelled and purified from unbound dye prior to their association, but even the site-specific installation of a fluorescent reporter disrupts complex association to a greater or lesser extent. Here, we label preformed protein complexes with a latent fluorophore. Because only labelled proteins and protein complexes are fluorescent, no purification steps are required, and the heterogeneous mixture of fluorescently labelled species are analysed directly with diffusion spectrometry.

At alkaline pH, and in the presence of a thiol (here, β-mercaptoethanol, BME), primary amines exposed on the surface of proteins and protein complexes react with o-phthalaldehyde (OPA) to form a bicyclic, isoindole-type fluorophore in situ [15, 16]. Though the fast kinetics of this process were initially observed [2], its application to the analysis of protein mixtures has been generally limited to efforts aimed at post or precolumn peptide derivitization [13, 17], or the quantitative detection of small quantities of amino acids within biological tissue [21, 6].

Example Device of the Invention

FIGS. 1a and 1b are illustrations of a microfluidic device according to one embodiment of the invention. FIG. 1a is a 3D representation of a device in use. having a component fluid flow and blank fluid flows, with inset images of the distribution of analyte at the nozzle, as well as three measurement points, at 1 mm, 3 mm and 9 mm from the start of the small cross section channel as described below. FIG. 1b is a plan view of the device.

FIG. 1a shows the diffusion of a mixture of bovine serum albumin and beta lactoglobulin in the small cross section channel.

A device 1 for use in the present invention may include a component fluid flow supply channel 2 which contacts a blank fluid flow supply channel 3a at a junction within a nozzle, which is a large cross section channel 4. In preferred embodiments, two blank fluid flow supply channels 3a and 3b are provided, as shown in FIG. 1b. The component fluid flow supply channel 2 may be in fluid communication with an upstream component fluid reservoir 5, which may include or be part of a controllable syringe (not shown). Each blank fluid flow supply channel 3a and 3b may be in fluid communication with an upstream blank fluid reservoir 6, which may include or be part of a controllable syringe (not shown). One reservoir 6 may supply two blank fluid flow channels 3a and 3b.

Downstream from and in fluid communication with the large cross section channel is a small cross section channel 7. The small cross section channel 7 may have a meandering (convoluted) path, as shown in FIG. 1b. The small cross section channel 7 is adapted for use with an analytical detector (not shown) which may be arranged to analyse components in a fluid present in the channel at one or more locations along the small cross section channel 7. The analytical detector may be arranged to simultaneously detect components in a fluid across two or more sections of the small cross section channel, as shown illustratively by the detection zone 8.

The small cross section channel may be in fluid communication with a downstream collection reservoir 9.

The large cross section channel 4 typically has a cross section that is ten times that of the small cross section channel 7. Thus, in FIG. 1a, the inset images show the width of the small cross section channel 7 to be 300 µm (this is apparent in the 9 mm image, where the component has diffused to the edge of the blank fluid flow, where the fluid contacts the channel wall). The large cross section channel 4 has a largest width of 3,000 µm.

The large cross section channel 4 has a region of constant width extending from the junction. The channel then tapers (at an angle of ca. 60° to the fluid flow direction) until the channel is the width of the small cross section channel 7. The length of the large cross section channel 7 from the junction (where the component fluid supply channel and blank fluid supply channels meet) to the start of the small cross section channel 7 may be around 100 µm.

The width of the small cross section channel 7 remains substantially constant throughout its path. The length of the small cross section channel 7, beginning from the point where the large cross section channel 4 finishes to the reservoir 9, may be in the region of 10 mm.

The device of the invention is used to analyse the radii of a component such as a polypeptide, and preferably the individual radii of components, in a fluid. The component fluid is provided as a flow in a fluidic device and the diffusion of each component in the fluid flow into a neighbouring blank fluid flow is measured. The blank fluid is a fluid that lacks the component.

The fluidic device 1 may be prepared using standard soft-lithography techniques using, for example, polydimethylsiloxane as the base material. Suitable photoresists may be prepared according to the desired shape and dimensions of the fluid flow channels and reservoirs.

In use, a component fluid is provided into the reservoir 5 and permitted to flow through the component fluid supply channel 2 to the large cross section channel 4, where it contacts blank fluid flows. The blank fluids are provided into the reservoir 6 and permitted to flow through the component fluid supply channels 3a and 3b to the large cross section channel 4. The flow rate may be controlled by syringe pumps which supply the supply channels 2, 3a and 3b. Alternatively, the flow is a gravity feed of the fluid from the reservoirs 5 and 6.

The component fluid flow and the blank fluid flows contact in the large cross section channel 4 and form a laminar flow of the component fluid flow in between the blank fluid flows. The flows are permitted to flow downstream into the small cross section channel 7 from the large cross section channel 4. Components within the component fluid flow are permitted to diffuse from the component fluid flow into the blank fluid flows. The diffusion of the components may be measured at one or more locations along the small cross section channel 7, for example in the detection zone 8. Typically the first measurement is taken before a component (such as the smallest component) has reached the edge of the blank fluid flow, where the fluid contacts the channel wall. Once the appropriate number of diffusion measurements is made, the fluid flows may be collected in a reservoir 9, or may be permitted to flow into a second analytical device, which is in fluid communication with the fluid device 1. The diffusion profiles over the length of the small cross section channel 7 are shown in FIG. 1a, where the white components are seen to diffuse into the darker blank fluid flow.

The inventors have established that the use of a large cross section channel in fluidic device for detecting component diffusion, provides certain benefits that allow the radii of components in a fluid to be more accurately determined. Use of the device results in a well-defined initial configuration for the components in the component flow from the point where the component flow and the blank flow enter the small width channel 7. The use of a large flow channel 4 minimises the diffusion of components prior to the establishment of a constant velocity profile across the channel downstream, for example in the small cross section channel 7, where the diffusion measurement are undertaken.

Figure 4:
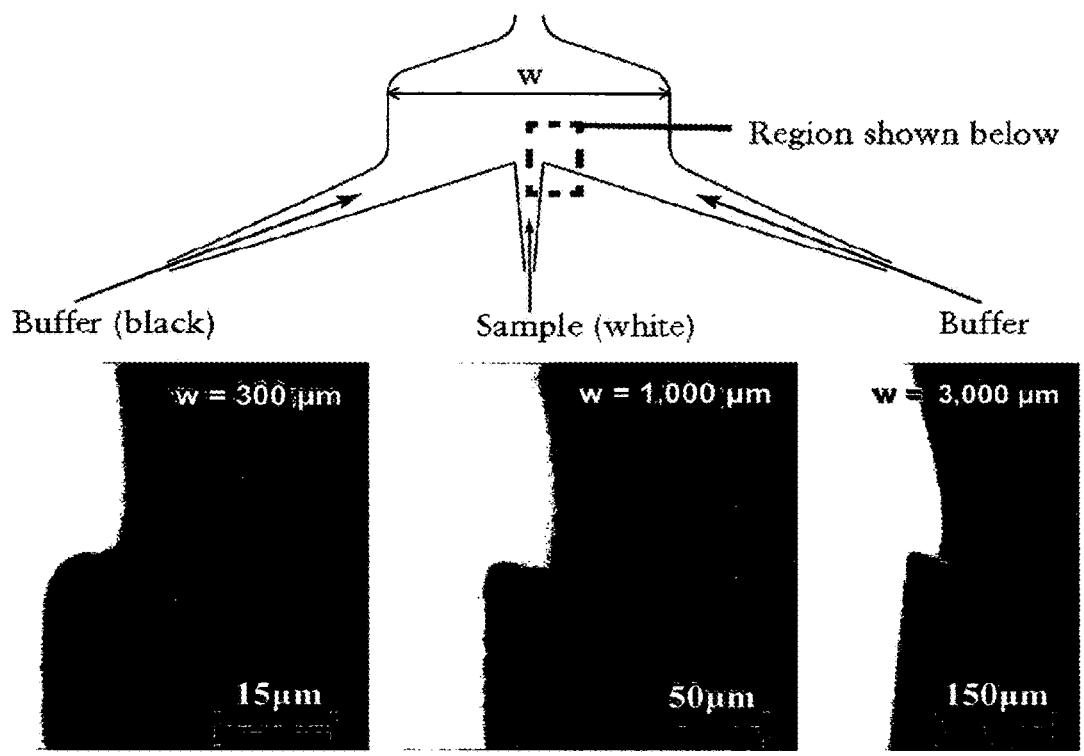
FIG. 4 shows the junction, the point where a component fluid flow (white) meets two blank fluid flows (black), in three different nozzles, or large cross section channels, having the widths from left, 300 μm, 1,000 μm and 3,000 μm, where the width refers to the largest cross section in the nozzle, which is ten times wider than the width of the component fluid flow at the junction (i.e. having widths of 30 μm, 100 μm and 300 μm). The large cross section channel allows a clean and defined component flow to be established, having a reduced residency time (reduced stagnation) at the junction. The flow rate is 4 μLh$^{-1}$ and the component is a colloid with a radius of 25 nm.

FIG. 4 shows that the use of a large cross section channel, ten times wider than the small cross section channel, results in a clean and defined component flow. In FIG. 4, three images are shown of a component fluid flow (white) entering a large cross section channel from a component fluid supply channel. The component fluid flow in the large cross section channel is seem to be relatively clean and defined from the point at which the component fluid first contacts the blank fluid flow (grey).

A worked example describing the preparation of the microfluidic device of FIGS. 1a and 1b is set out below in the Alpha-B Crystallin experiments.

Analysis of Multi-Component Mixture

An aqueous mixture comprising equal amounts (0.02% by volume) of 25 nm and 100 nm colloids was analysed using the microfluidic device described above, individual solutions of each of the colloids were also prepared. Solutions were flowed through the device at 40 µLh$^{-1}$, and illuminated at 480 nm using an LED light source. Three 10 s exposures were taken using a high quantum-yield CCD camera, one at each of the three measurement points.

Figure 2:
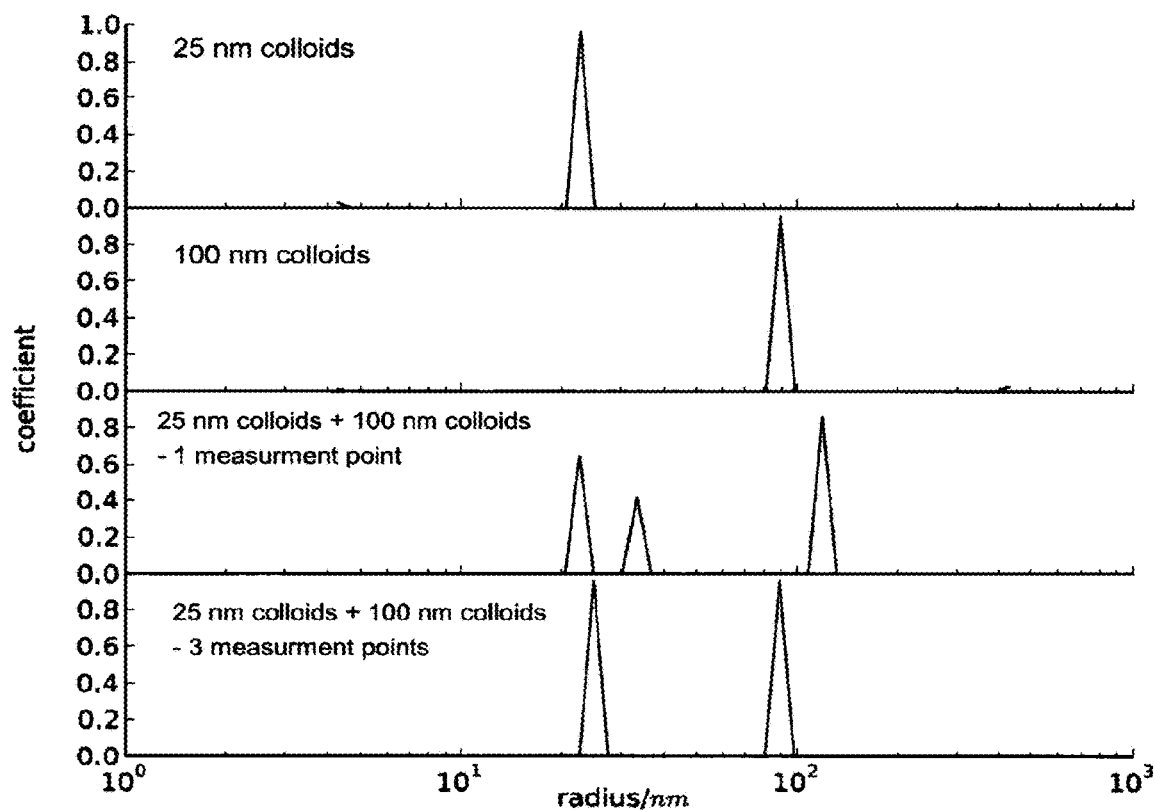
FIG. 2 includes graphs relating to the calibration of the fluidic device of FIG. 1 using a 50:50 mixture (0.1% by volume) of fluorescently labelled components (colloids) with 25 nm and 100 nm radii. A: The size spectrum generated by a least squares analysis of the recorded distribution data with maximum entropy regularisation (bottom spectrum), and is compared to the size spectra of homogeneous solutions of each of these colloids (top and second from top spectra). Also shown here is a comparison between the size spectra generated from data recorded at three measurement points (bottom spectrum) and a single measurement point (second from bottom spectrum). The use of a plurality of measurement points provides resolved spectra having greater accuracy and greater resolution. B: The distribution of the component mixture at the three different measurement points at 1 mm, 3 mm and 9 mm along the channel, as well as the fits to these distributions generated by the least squares algorithm.
Figure 2:
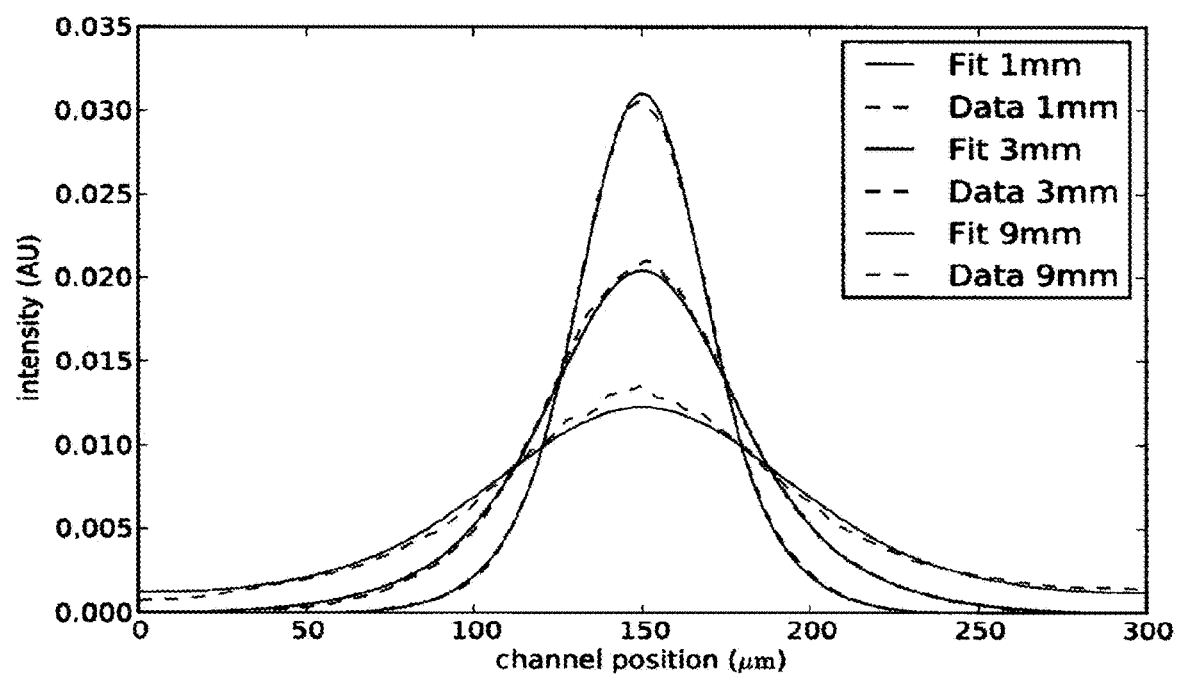

The diffusion profile was measured at three different diffusion times at 1 mm, 3 mm and 9 mm from the start of the small cross section channel (see FIG. 2, bottom graph). The combination of diffusion profiles was deconvoluted using a highest entropy regularisation approach as described herein, to show the presence of the two components having different hydrodynamic radii (FIG. 2, bottom spectrum), which very closely matched the experimentally derived values determined for the individual colloids (top and second from top spectra). For comparison, a deconvolution of a single diffusion profile was performed (second from bottom spectrum). As can been seen, this deconvolution erroneously suggested the presence of three different components in the mixture, where the component having a smaller radius was resolved as two separate signals. Moreover, the component having a larger radius was resolved as a signal having a higher radius. The use of multiple measurement points therefore provides greater accuracy and greater resolution in the deconvolution of diffusion profiles.

Microfluidic diffusion techniques may also be used to resolve multicomponent mixtures of proteins. A second calibration was performed on a mixture of the proteins glucagon, beta-lactoglobulin and bovine serum albumin (BSA). Each protein was prepared as a homogeneous solution in phosphate buffer containing 20% DMSO, as well as a 1:1:1 mixture (by mass) of the three proteins, DMSO was used to ensure that all of the proteins remained in the monomeric state during the experiment, and that no unknown complexes were formed.

The three proteins were fluorescently labelled. Here, preformed protein complexes were labelled with a latent fluorophore, i.e. one which is fluorescent only when bound, and not detected if free in solution. Because only labelled proteins and protein complexes are fluorescent, no purification steps are required, and the heterogeneous mixture of fluorescently labelled species can be analysed directly with diffusion spectrometry. At alkaline pH, and in the presence of a thiol (here, p-mercaptoethanol, BME), primary amines exposed on the surface of proteins and protein complexes react with o-phthalaldehyde (OPA) to form a bicyclic, isoindole-type fluorophore in situ.

Figure 6:
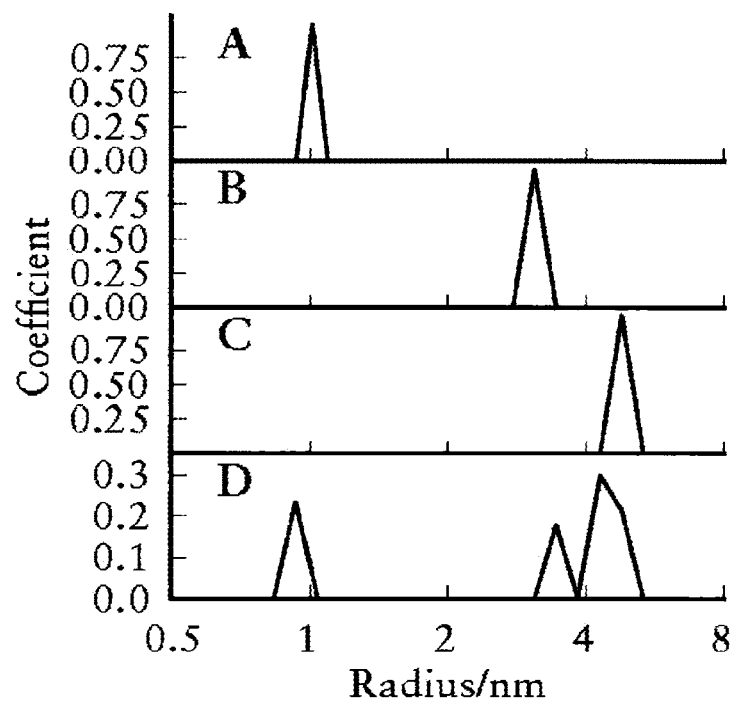
FIG. 6 shows the size distributions, expressed as hydrodynamic radii, of A, Glucagon, B, Beta lactoglobulin, and C, BSA, in individual homogeneous solutions and D, as a 1:1:1 mixture of all three species. Samples were illuminated at 365 nm using an LED light source on an inverted microscope, and detected with a high quantum-yield CCD camera.

The diffusion experiments were performed in the same manner as above. The illumination wavelength used in the experiments was 365 nm. FIG. 6 shows the results of the diffusion measurement on the individual and combined test solutions. Three species are resolved in the mixture at sizes similar to those in the homogeneous solutions, although the peaks corresponding to beta lactoglobulin and bovine serum albumin are shifted slightly closer together. This is likely to be an effect of the random and systematic errors in the experiment, and these two peaks are approaching the resolving power of microfluidic diffusion experiment at this level of signal-noise.

Analysis of BSA

When characterising monodisperse solutions such as single proteins, microfluidic diffusion techniques have the potential to be extremely precise. As a demonstration, microfluidic diffusion was used to study the change in hydrodynamic radius of the protein bovine serum albumin (BSA) dissolved in pH 7 buffer and dissolved in the same buffer with 80% DMSO.

BSA at 5 mg/mL was dissolved in pH 7 phosphate buffer (e.g. 5 mM HEPES buffer), before labelling with OPA in the presence of β-mercapto ethanol (BME). The standard labelling mixture was a solution of 12 mM OPA, 18 mM BME, 4% SDS, and 200 mM carbonate at a pH in the range 9.5-10.5. The solution was prepared in advance and mixed in a 1:1 volume ratio with the protein solution.

This stock solution of labelled BSA was then diluted to 1 mg/mL in the same buffer and in DMSO (with a final DMSO concentration of 80% by volume). The hydrodynamic radius for BSA in each of the solutions (buffer and 80% DMSO) was measured using the experimental techniques identical to that for the multi-component mixture detailed above.

FIG. 7 shows the diffusion coefficients calculated for each of the BSA solutions. The diffusion coefficient of the BSA in aqueous buffer corresponds to a hydrodynamic radius of 3.5 nm, comparable with literature values. In 80% DMSO, the protein is unfolded dramatically, with a hydrodynamic radius of 6±0.5 nm.

Analysis of Insulin Aggregation Events

The methods of the invention may be used to study the coexistence of insulin in monomeric, dimeric and hexameric forms, insulin (available from commercial sources) may be covalently labelled at physiological pH. The change in the composition of an insulin sample may be measured over time. Thus, aliquots may be removed from the sample and tested using a diffusion method of the invention. Changes in the diffusion profile may be linked to changes in the composition of the sample, for example increased aggregation. Changes in the aggregation may also be monitored with changes in the pH of the insulin sample. For example, aggregation may be determined at pH 2 and pH 4. The populations of various species in the samples may be compared.

Analysis of Aβ(1-42) Aggregation Events

Diffusion spectrometry may be used to analyse highly heterogeneous mixtures of protein complexes. A particularly challenging type of biomolecular association process for study is that of the formation of aberrant β sheet-rich aggregates: commonly known as amyloid fibrils. Amyloid-β, particularly in oligomeric form, has been implicated as one of the main pathogenic factors in Alzheimer's disease. Obtaining a size distribution for the protein solution as it undergoes aggregation is important to understanding both the pathology of the disease and the mechanisms underlying the aggregation.

Size distributions for amyloid aggregates are commonly obtained using atomic force microscopy. However, AFM techniques generally require the concentration of the sample to be lowered, meaning that dynamic complexes may dissociate before a measurement can be performed. AFM also has problems in finding a true size distribution in that the distribution of analyte over a surface is rarely uniform. Diffusion spectrometry is a bulk technique, and diffusion times are short enough that the composition of the sample solution should remain unchanged throughout its passage along the diffusion channel, indeed, each molecule spends only on the order of 10 or 20 seconds inside the device. Furthermore, the species for analysis are only diluted by at most a factor of ten, which minimises dissociation.

Figure 3:
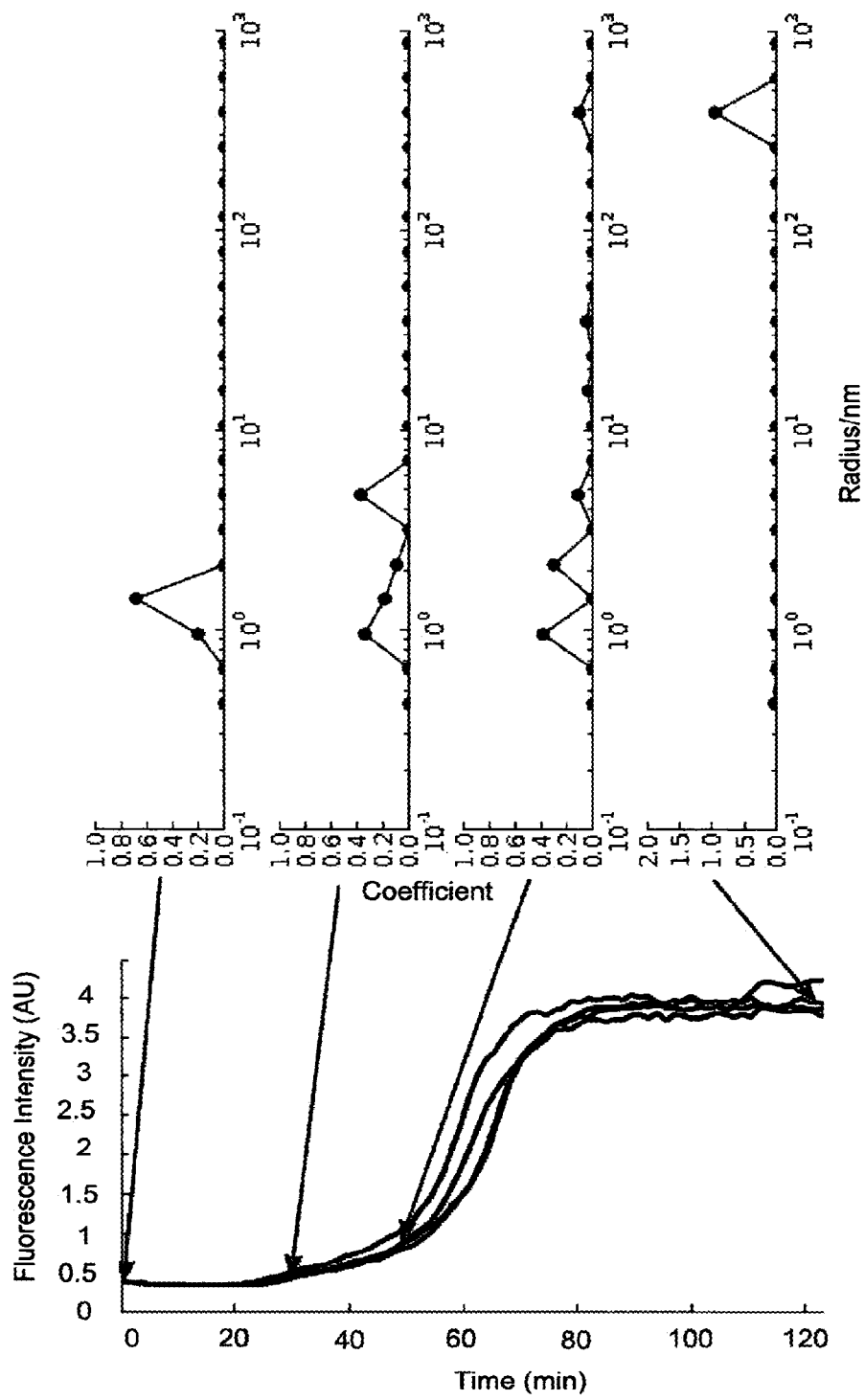
FIG. 3 shows the size distribution of Aβ(1-42) aggregates growing from monomer over 120 minutes. A: ThT fluorescence intensity over time—aliquots of sample were taken at 0 minutes—before any aggregation, at 30 and 50 minutes—before and during the growth phase, and at 120 minutes after monomer had been depleted. B: The size distributions found using least squares fitting with maximum entropy regularisation. The solution is initially monomeric, before forming oligomers, fibrils, and eventually macroscopic fibril "clumps".

FIG. 3 shows the size distribution of Aβ (1-42) aggregates at four different time points in an aggregation reaction starting from monomeric protein. The details of the diffusion measurements are identical to those for the other protein solutions detailed above, although an exposure time of 100 s was used at each measurement point rather than 10 s.

At the beginning of the reaction the peptide is monomeric, as expected. Interestingly, a peak of larger species begins to appear only 30 minutes into the time-course, before ThT fluorescence intensity has increased appreciably. These larger species have a size range spanning oligomers to small fibrils, and given the lack of associated ThT signal it seems likely that much of the peak comprises the small, ThT negative oligomers thought to be associated with disease. After 50 minutes, at the beginning of the growth phase of the reaction, there is still a significant fraction of monomer, as well as the previously observed mixture of oligomers and fibrils. There are now significant populations of fibrils at larger sizes up to about 20 nm in hydrodynamic radius, and it is at this time point that the appearance of aggregates fibrils first occurs (the peak at around 400 nm). By the time ail of the monomer has been consumed, at 120 minutes, all of the aggregates are contained in these large clumps of fibrils.

Experimental

Aβ(1-42) was cloned into the "PetSacKan" plasmid, recombinantly expressed in *E. coli* BL21 cells, and purified in batch mode using anion exchange chromatography. This procedure allowed for the production of large quantities of peptide at relatively high purity. The resulting peptide was divided into 1 mL aliquots, lyophilized, and stored at −20° C. until further use. Although obtaining reproducible kinetic data for the aggregation of the Aβ(1-42) peptide has historically been challenging [10], it has recently been shown that performing a size exclusion chromatography step to separate pure protein monomer from oligomeric intermediates immediately prior to the aggregation reaction markedly improves the quality of the kinetic data obtained [9]. Accordingly, a single aliquot was solubilized in 6 M guanidinium chloride and passed through a Superdex 75 10/300 gel filtration column. The oligomer "shoulder" which eluted just before the protein monomer peak was rejected, and pure monomer which eluted between approximately 13 and 15 mL was collected.

Approximately 1.3 μM protein monomer in 20 mM sodium phosphate buffer, pH 8.0, 200 μM EDTA, and 0.02% sodium azide was eluted and kept on ice.

A thioavin T (ThT) kinetic assay was used to monitor the process of fibrillation, with 4 replicates of 1.2 μM Aβ(1-42), 20 μM ThT, in the above buffer. Fibrilisation was monitored in real time, and at time points corresponding to the beginning of the aggregation reaction, the end of the lag time, the early part of the growth phase, and the establishment of the equilibrium phase, aliquots were removed from 4 additional wells and combined with 10 μL of an OPA-BME labelling stock, also in the above kinetics buffer. The aliquots, which contained approximately 1.0 μM Aβ (1-42), 600 μM OPA, and 900 μM BME, were kept on ice and then rapidly analyzed in the diffusion devices.

Analysis of Alpha-B Crystallin

Alpha B-crystallin oligomerisation was studied by diffusion spectroscopy.

Even though still under debate [22], a broad consensus has emerged, that alpha B-crystallin in its native state assembles as oligomers ranging in size from 10 to 40 subunits [23], and the dynamics of the oligomerisation equilibrium might be of crucial importance to the protein function, it is this heterogeneity that has complicated the study of the protein. There is some structural information on the crystalline domain from a truncated variant claiming that the oligomer consists of dimeric, 7-stranded β-sheet building blocks [24], and attempts to describe the polydispersity of alpha B-crystallin oligomers were successfully accomplished by mass spectrometry [23], [25], [26]. However, so far it has not been possible to trace monomeric species in significant quantities within polydisperse mixtures.

Alpha B-crystallin was expressed and purified as described below. After the last purification step the identity of alpha B-crystallin was verified by SDS-PAGE (see FIG. 8(*a*)). A single band at 20 kDa confirmed the presence of monomeric, pure alpha B-crystallin under denaturing conditions. Further proof of the purity of alpha B-crystallin was obtained by mass spectrometry (FIG. 8(*b*), upper panel). The experimental mass of 20,160 Da was found to very closely match the expected, theoretical mass of 20,159 Da.

For the diffusion spectroscopy experiments alpha B-crystallin was labelled with ortho phthalaldehyde (OPA), as described above. Complete labelling was proven with mass spectrometry (see FIG. 8(*b*), lower panel). The shift in m/z of approximately 2,200 Da corresponds to OPA-labelling of 12.5 amines, nearly matching the complete labelling of 10 primary amines and the N-terminal amine in the sequence of alpha B-crystallin. DLS and glass nanopore analyses (further described below) were conducted with unlabelled alpha B-crystallin.

Alpha B-crystallin was sized using diffusion spectroscopy in order to identify monomeric as well as different oligomeric protein populations. The diffusion device used is described in further detail below. The diffusion data at different measurement points was plotted as fluorescence intensity along the microchannel yielding a diffusion profile (FIG. 9(*a*)), and the experimental data was fitted to a theoretical model as described herein resulting in the size distribution for alpha B-crystallin (FIG. 9(*b*)). Indeed, two populations were resolved by diffusion spectroscopy: a small population of a species with a mean hydrodynamic radius of approximately 2 nm and a larger population of a species with a mean hydrodynamic radius of around 7 nm.

The small population, making up less than 20% of the mixture, represented monomeric alpha B-crystallin, and the highly abundant population accounting for more than 80% of the sample included oligomeric forms of the protein. No conclusions on the oligomeric distribution were possible. However, the low size species was identified as an isolated species in significant quantities for the first time, and the quantification of the relative populations of the two species allow the study of the alpha B-crystallin oligomerisation equilibrium.

For comparison, label-free 30 μM alpha B-crystallin was analysed with DLS. A broad size distribution, overlapping with the size distribution measured by diffusion spectroscopy, was found to represent oligomeric alpha B-crystallin (FIG. 10). The good agreement of both techniques suggested that there was no direct impact of the covalent label on the oligomerisation. However, using DLS no signal was detected for the low size species at 2 nm. As larger particles scatter significantly more light, intensities measured by DLS were biased towards oligomeric proteins, and thus large oligomers might potentially have masked small, weakly scattering monomeric alpha B-crystallin. Therefore, DLS is not a suitable technique to investigate the oligomerisation equilibrium of alpha B-crystallin.

A further attempt to quantify the monomer-oligomer equilibrium of label-free alpha B-crystallin was made using single molecule detection through a glass nanopore (in collaboration with Nicholas Bell and Dr Ulrich Keyser at the Cavendish Laboratory, University of Cambridge). The technique, and its application to single protein molecule detection, is described in [27] and [28]. Due to the co-existence of monomeric and oligomeric alpha B-crystallin in the sample, a bimodal distribution of events was expected as translocation characteristics of the polydisperse sample through the glass nanopore. Prior to the measurement the pH of the sample was adjusted to 10.5 in order to prevent stickiness and adherence to the sides of the glass nanopore and to ensure ballistic travel of the proteins through the nanopore. Electro-osmotic flow occurred on application of a voltage of −500 mV across the pore, and the transport events were recorded.

The spikes in the ionic current traces (FIG. 11 (a)) illustrated ionic current change events, and thus reflected the passage of single analyte molecules through the nanopore. The scattered heat map (FIG. 11 (b)) of the mean event current versus the event duration—where the colours represented the number of translocations—showed a cluster of events at the filter cut-off time (approximately 10 μs for the 50 kHz filter), the event duration limit imposed by the filter frequency. Most of the translocations were close to the detectable threshold, but nevertheless the main clustering was likely to correspond to ballistically traveling proteins, as was reported for single, monodisperse protein samples [28]. The presence of protein was detected without doubt, but with the current resolution the assignment of translocation events to monomeric and oligomeric populations remained unfeasible due to overlapping translocation statistics.

The impact of the monomeric protein concentration on the oligomerisation equilibrium of alpha B-crystallin was also studied by diffusion spectroscopy. The relative populations of monomeric and oligomeric alpha B-crystallin were examined using MFD with the monomeric concentration ranging from 15 μM to 125 μM. Independent of the protein monomer concentration two species were identified in all assays. The smaller species with a mean hydrodynamic radius of around 2 nm made up 10-20% of the mixture, and the species with 7 nm radius displayed a relative abundance of 80-90%.

The relative population of the monomer to oligomer was not seen to depend on the initial monomer concentration. Given the error of the method, the small relative changes in abundance signify that in the order of the examined monomer concentrations, there is no considerable impact of the monomeric concentration on the oligomerisation equilibrium.

Sizing of alpha B-crystallin revealed two distinct species with differing hydrodynamic radii, representing the heterogeneity of the sample. The mean hydrodynamic radii of approximately 2 nm and 7 nm for monomeric and oligomeric proteins, respectively, were in good agreement with previously published data. The very sensible value of the average oligomer radius of 7 nm agreed well with data from mass spectrometry [26], electron microscopy [22], small-angle x-ray scattering and solid-state NMR [29].

Microfluidic diffusion spectrometry may be used to identify, in a single measurement, monomeric alpha B-crystallin as an isolated species with a small hydrodynamic radius coexisting with oligomeric forms of the protein. This resolution of species was found to be unique to diffusion spectrometry, since neither DLS nor nanopore experiments reveal the presence of the monomeric species. In DLS the bias towards larger, higher scattering particles obscured the presence of smaller sized particles, and the present nanopore techniques are not sensitive enough to detect a bimodal distribution of events as expected for a mixture of monomer and oligomer populations. Moreover, previous attempts to describe the size distribution of the chaperone with mass spectrometry resulted in a detailed description of the individual populations of oligomers without tracking the monomer ([25] and [26]).

Experimental

The plasmid encoding the gene for human alpha B-crystallin was kindly supplied by Andrew Baldwin (University of Oxford, United Kingdom).

Protein Expression and Purification. The plasmid encoding the gene for human alpha B-crystallin was transformed to competent *E. coli* BL21 (DE3) cells (Invitrogen). Overnight Express Instant TB Autoinduction Medium (500 mL, Novagen) supplied with 1% (v/v) glycerol and 100 μg/mL kanamycin was inoculated with 12 mL of an overnight culture of the transformed cells. Protein overexpression was induced overnight, vigorously shaking at 30° C. Cells were harvested by centrifugation (6000 g, 15 min, 4° C.) and re-suspended in 20 mM Tris-HCl, pH 8.3 (20 mL/500 mL culture) containing 1 mg/mL lysozyme (Sigma-Aldrich), a complete EDTA-free protease inhibitor cocktail tablet (Roche) and a spatula tip DNaseI (Roche) per 500 mL culture medium. Cells were lysed by sonicating 20×15 s using an output of 6 on an Ultrasonic Processor XL sonicator (Misonix). The lysate was centrifuged (18,000 g, 30 min, 4° C.) to remove cell debris, and filtered through a 0.45 μm syringe. Filter (Millipore). The filtered lysate was loaded on a Q sepharose column (GE Healthcare) pre-equilibrated with 20 mM Tris-HCl (pH 8.3) and eluted by a linear gradient elution from 0 to 200 mM NaCl over 4 column volumes. The protein containing fractions were applied onto a HiLoad 26/600 Superdex 75 pg gel filtration column (GE Healthcare) for final purification in 20 mM NaPi (pH 8.5) and eluted at a flow rate of 1 mL/min. The identity of the protein containing fractions was checked with SDS-PAGE and MALDI-MS.

Microfluidic Device Fabrication. SU-8 3025 photoresist (Microchem) was spin-coated for 7 s at 500 rpm and for another 30 s at 3000 rpm onto silicon wafers. The spin-coated wafers were soft-baked on a hotplate at 95° C. for 12 min, then lined with the mask, and exposed to UV light for 15 s. Following exposure, the wafers were baked for another 5 min before development of the mold using PGME. PDMS stamps were produced by pouring liquid pre-polymer (10:1 (v/v) silicone elastomer:crosslinker) blackened with carbon nanopowder (Sigma Aidrich) over the mold and curing it for 2 h at 60° C. The PDMS stamps were cut out with a scalpel and after punching inlet and outlet holes with a biopsy needle, the stamps were exposed to an air plasma for 10 s ($O_2$ partial pressure 4.0, power 4.0) and bonded to glass coverslips (ground-edges 90°, Thermo Scientific). The device was formed with channels having a height of 25 Mm, and widths ranging from 1,000 (for example, at the large cross section channel) to 10 μm.

Microfluidic Diffusion Spectrometry. Human alpha B-crystallin was labelled using an ortho-phthalaldehyde (OPA) dye solution (200 mM $NaHCO_3$ (pH 10.5), 60 mM ortho-phthalaldehyde, 90 mM β-mercapto ethanol) at a 10- to 20-fold excess of OPA with respect to primary amines. Buffer solution and fluorescently labelled proteins were added in the respective inlets using gel-loading pipet tips, and tubing connected to a 250 μL glass syringe (Hamilton) was fitted to the flow outlet. A neMESYS syringe pump (Cetoni) was used to set the total withdrawal flow rate to 80 μL/h. OPA-labelled alpha B-crystallin was excited with UV light and imaged at 10-fold magnification with a 49000—ET—DAPI filter cube (Chroma Technology Corp) on an Axio Observer. D1 microscope (Zeiss) using an Evolve 512 EMCCD camera (Photometries). The image data were fitted to linear superpositions of a set of basis functions describing the distributions of solutions of homogeneous particles ranging from 0 nm to 800 nm in diameter at distances corresponding to three fluorescent measurement points (at 1, 3 and 9 cm).

Dynamic Light Scattering (DLS). Dynamic light scattering experiments were conducted using a Zetasizer Nano ZSP (Malvern Instruments) with backscatter detection at a scattering angle of 173°. The viscosity and the refractive index of water were used as parameters for the buffer solution, and the material properties of the analyte were set to protein. All samples were filtered through a 0.22 μm Millex syringe filter (Millipore) before analysis. The data were analysed using the "multiple narrow" mode of the Malvern instrument software to deconvoluted the correlation function into a size distribution.

Nanopore Detection Measurements. The experiments were performed in collaboration with Nicholas Bell and Ulrich Keyser at the Cavendish Laboratory, University of Cambridge as previously described in [28]. The measurements were made with alpha B-crystallin at a concentration of 1 μM at pH 10.5.

MALDI Mass Spectrometry. The mass of the unlabelled and the GPA-labelled alpha B-crystallin was measured by MALDI mass spectrometry (Dr Len Packman at the PNAC Facility, Department of Biochemistry, University of Cambridge). The theoretical molecular mass of 20,159 Da was used for comparison with the experimental masses for the unlabelled and labelled alpha B-crystallin.

Protein Concentrations. Monomeric protein concentrations were calculated by measuring the absorbance of monomeric material at 280 nm, using a molar extinction coefficient of 13,980 $M^{-1}$ $cm^{-1}$.

Analysis of Liposomes

Differently sized liposome structures were studied by diffusion spectroscopy.

The size of liposomes has been shown to be crucial for the characteristics of artificial biomembrane systems and for appropriate pharmacokinetics in drug delivery [30]. In recent years, different methods to size vesicles have been discussed in the literature: electron microscopy [31], analytical ultracentrifugation [32], analytical size exclusion chromatography [33], flow field-flow fractionation [34], enzymatic lipid quantitation assays [35] and dynamic light scattering (DLS) [36], with DLS being the technique of choice on the strength of the ease of use. However, accurate reliable and reproducible sizing of lipid vesicles particularly in complex heterogeneous liposome mixtures remains challenging due to the requirement of sophisticated instrumentation or technical limitations. Microfluidic diffusion spectroscopy was used to determine the size of fluorescently labelled liposomes and to resolve the sizes of vesicles in a mixture of liposomes with different sizes.

Homogeneous solutions of fluorescent liposomes, 30 nm and 100 nm in extrusion pore diameter, were prepared for sizing as well as a 1:1 mixture of the two. Microfluidic diffusion spectrometry was used to analyse the liposomes and calculate their sizes. For all samples the fluorescence intensity along the micro-channel at three measurement points each corresponding to a different diffusion time was measured to yield the diffusion profiles (FIGS. 13 (a), (c) and (e)). A microfluidic fluidic device as described above was used.

The small vesicle extruded through a membrane with 15 nm pore radius diffused faster than the larger vesicles extruded to 50 nm radius (as expected from the Stoked-Einstein relationship). At every measurement point the smaller vesicle had spread more extensively through the channel, and the fluorescence intensify at the initial inlet position in the middle of the channel decreased more rapidly in the case of the smaller liposome. The best fit size distributions (FIGS. 13 (b), (d) and (f)) were obtained by least squares fitting of the diffusion profiles with linear superpositions of basis functions describing the diffusional behaviour of particles of defined sizes.

A good fit was confirmed by low chi-squares values of 0.05, 0.14 and 0.06 for the vesicles extruded to 30 nm, 100 nm and a mixture of the two, respectively. The mean hydrodynamic radius of the liposomes extruded through a filter with pores of 15 nm radius was determined to be 22 nm, and the liposomes with 50 nm extrusion-radius were found to have a mean hydrodynamic radius of 45 nm. The analysis of the mixture revealed separate populations of both species with clear separation of the two.

The DLS measurement of the same samples revealed results in the same order for the mean hydrodynamic radii of the liposomes: 27 nm for the vesicles extruded to a radius of 15 nm and 53 nm for the vesicles extruded to a radius of 50 nm. However, the size distributions found by DLS were broadly distributed, which made it difficult to reliably detect two distinct peaks in a mixture. Whilst microfluidic diffusion explicitly differentiated between the two liposome species in the mixture without any a priori information, DLS identified two partially overlapping peaks only when biasing the analysis towards a heterogeneous sample. Without any a priori information on the polydispersity of the sample a single, remarkably broad peak with a mean size that was slightly shifted from the mean radius of the larger vesicle towards the mean radius of the smaller vesicle was found (data not shown), in that case the accuracy of discrimination was very poor and the limits of detection were reached. Unlike DLS, diffusion spectroscopy is not biased towards larger, higher scattering particles, it is believed that the accuracy of the recorded hydrodynamic radii of the liposomes may be improved with further adaptations of the diffusion measurement techniques described herein.

As with the experiments described above in relation to Alpha-B Crystallin, microfluidic diffusion measurement techniques allow for sizing of particles in complex polydisperse mixtures. The diffusion measurements are characterised in that they have a considerably low sample consumption, enhanced sensitivity and reproducibility, and the sizing of particles in heterogeneous mixtures occurs without significant biasing towards species with large hydrodynamic radii.

Experimental

Preparation of Fluorescent Liposomes. 1,2-dioleoyl-sn-glycero-3-phosphoethanol-amine-N-carboxyuorescein (PE CF) fluorescent lipids in chloroform (Avanti Polar Lipids) were used as fluorescent labels for the liposomes used in the sizing experiments. The chloroform was evaporated using dry nitrogen to yield a lipid film. The film was subsequently re-suspended in double distilled water, frozen in liquid nitrogen and lyophilised overnight for drying. The dry fluorescent lipids were re-suspended to a final content of 10% fluorescent lipids in 1 mM dimyristoylphosphatidylcholine (DMPC) lipids (Avanti Polar Lipids) in 20 mM NaPi, 0.01% $NaN_2$, and the suspension was stirred thoroughly for 1 h at room temperature. The resulting large multilamellar vesicles were disrupted by five freeze-thaw cycles, and differently sized unilamellar vesicles were prepared by extrusion through polycarbonate membrane filters with pores of different sizes (Avanti Polar Lipids) using an Avanti Mini-Extruder (Avanti Polar Lipids). Liposome stock solutions of 500 μM were prepared using extrusion filters with pore diameters of 30 nm and 100 nm diameter. The actual measurement concentration was 250 µM with 25 µM fluorescent lipids.

Microfluidic Diffusion Spectrometry.

The diffusion device was filled with buffer solution (20 mM NaPi, 0.01% NaN$_2$), and fluorescently labelled vesicles were added in the respective inlet. A neMESYS syringe pump (Cetoni) was used as before to set the total withdrawal flow rate to 80 µL/h. The fluorophores incorporated into the liposomes were observed with an ET-GFP filter cube (model 49002, Chroma Technology) on an Axio Observer.D1 microscope (Zeiss) using an Evolve 512 EMCCD camera (Photometries). The image data were fitted to linear superpositions of a set of basis functions as described above.

Dynamic Light Scattering (DLS). Dynamic light scattering experiments were performed as described above.

REFERENCES

All documents mentioned in this specification are incorporated herein by reference in their entirety.

[1] J. Atencia and D. J. Beebe. Nature, 437(7059):648-655, 2004.
[2] James R. Benson and P. E. Hare. Proceedings of the National Academy of Sciences of the United States of America, 72:619-622, 1975.
[3] J. P. Brody and P. Yager. Sensors and Actuators A: Physical, 58(1):13-18, 1997.
[4] C D. Costin, R. K. Olund, B. A. Staggemeier, A. K. Torgerson, and R. E, Synovec. Journal of Chromatography A, 1013(1):77-91, 2003.
[5] C. T. Culbertson, S. C. Jacobson, and J. Michael Ramsey. Talanta, 56(2):365-373, 2002.
[6] G. H. Fisher, L Arias, I. Quesada, S. D. D'Aniello, F. Errico, M M Di Fiore, and A. D'Anieilo. Amino Acids, 20:163-173, 2001.
[7] A. Hatch, E. Garcia, and P. Yager. Proceedings of the IEEE, 92(1):126-139, 2004.
[8] A. Hatch, A. E. Kamholz, K. R. Hawkins, M. S. Munson, E. A. Schilling, B. H. Weigl, and P. Yager. Nature Biotechnology, 19(5):461-465, 2001.
[9] Erik Hellstrand, Barry Boland, Dominic M. Walsh, and Sara Lisne. ACS Chemical Neuroscience, 1:13-18, 2010.
[10] Peter Hortschansky, Volker Schroeckh, Tony Christopeit, GiorgiaZandomeneghi, and Marcus Fandrich. Protein Science, 14:1753-1759, 2005.
[11] A. E. Kamholz, E. A. Schilling, and P. Yager. Biophysical Journal, 80(4):1967-1972, 2001.
[12] A. E. Kamholz and P. Yager. Biophysical Journal, 80(1):155-160, 2001.
[13] Enrique Mendez, R, Matas, and F. Soriano. Journal of Chromatography, 323:373-382, 1985.
[14] D. Qin, Y. Xia, and G. M. Whitesides. Nature protocols, 5(3):491-502, 2010.
[15] Marc Roth. Analytical Chemistry, 43:880-882, 1971.
[16] Marc Roth and Ayoub Hampai. Journal of Chromatography, 83:353-356, 1973.
[17] Hema S. Sista. Journal of Chromatography, 359:231-240, 1986.
[18] Dominic M. Walsh, Eva Thulin, Aedin M. Minogue, Niklas Gustaysson, Eric Pang, David B. Teplow, and Sara Lisne. FEBS Journal, 276:1266-1281, 2009.
[19] B. H. Weigl and P. Yager. Science, 283(5400):346, 1999.
[20] Y. Xia and G. M. Whitesides. Annual review of materials science, 28(1):153-184, 1998.
[21] David Zawieja, B. J. Barber, and Richard J. Roman. Analytical Biochemistry, 142:182-188, 1984.
[22] Peschek, J., Braun, N., Franzmann, T. M., Georgalis, Y., Haslbeck, M., Weinkauf, S. and Bucher, J. Proc Natl Acad Sci USA, 2009, 106, 13272-13277.
[23] Aquilinia, J. A., Benesch J. L., Bateman, O. A., Slingsby, C. and Robinson, C. V. Proc Natl Acad Sci USA, 2003, 100, 10611-10616.
[24] Laganowsky, A., Benesch, J. L., Landau, M., Ding, L., Sawaya, M. R., Cascio, D., Huang, Q., Robinson, C. V., Horwitz, J. and Eisenberg, D. Protein Sci, 2010, 19, 1031-1043.
[25] Baldwin, A. J., Lioe, H., Robinson, C. V., Kay, L. E. and Benesh, J. L. J Mol Biol, 2011, 413, 297-309.
[26] Baldwin, A. J., Lioe, H., Hilton, G. R., Baker, L. A., Rubinstein, J. L., Kay, L. E. and Benesh, J. L Structure, 2011, 19, 1855-1863.
[27] Bell, N. A. W., Engst, C. R., Ablay, M., Divitini, G., Ducati, C, Liedl, T. and Keyser, U. F. DNA Origami Nanopores. Nano Lett, 2011, 12, 512-517.
[28] Li, W., Bell, N. A. W., Hernandez-Ainsa, S., Thacker, V. V., Thackray, A. M., Bujdoso, R. and Keyser, U.F. ACS Nano, 2013, 7, 4129-4134.
[29] Jehle, S., Rajagopal, P., Bardiaux, B., Markovic, S., Kuhne, R., Stout, J. R., Higman, V. A., Klevit, R. E., van Rossum, B. J. and Oschkinat, H. Nat Struct Mol Biol, 2010, 17, 1037-1042.
[30] Litzinger, D. C., Busting, A. M., van Rookjen, N. and Huan, L. Biophys Acta, 1994, 1190, 99-107.
[31] Perevucnik, G., Schurtenberger, P., Lasic, D. D. and Hauser, H. Biochim Biophys Acta, 1985, 821, 169-173.
[32] McCracken, M. S. and Sammons, M. C. J Pharm Sci, 1987, 76, 56-59.
[33] Nozaki, Y., Lasic, D. D. and Tanford, J. A. Science, 1982, 217, 366-367.
[34] Moon, M. H. and Giddings, J. C. J Pharm Biomed Anal, 1993, 11, 911-920.
[35] Ingebrigtsen, L. and Brandi, M. AAPS PharmSciTech, 2002, 3, 9-15.
[36] Selser, J. C, Yeh, Y. and Baskin, R. J. Bioph J, 1976, 16, 337-356.
[37] Herling et al. Applied Physics Letters, 2013, 102, 184102.

The invention claimed is:

1. A method for determining the diffusion coefficient of two or more components, the method comprising the steps of:
   (i) providing a component fluid flow comprising two or more components;
   (ii) providing a blank fluid flow;
   (iii) flowing the component fluid flow and the blank fluid flow laminarly in a channel;
   (iv) measuring lateral diffusion of the two or more components from the component flow into the blank fluid flow at a plurality of diffusion times; and
   (v) comparing the measured lateral diffusion profiles of the two or more components from step (iv) with a series of distributions for components having known hydrodynamic radii, thereby determining a diffusion coefficient value for one of the two or more components from the lateral diffusion measurements of step (iv) and the hydrodynamic radius of each of the two or more components.

2. The method according to claim 1, wherein the lateral diffusion is measured at three or more diffusion times.

3. The method according to claim 1, wherein step (v) comprises deconvoluting the measured lateral diffusion profiles of the two or more components from step (iv) using a highest entropy regularisation approach with reference to a series of distributions for components having known hydrodynamic radii, thereby to determine the hydrodynamic radii for each of the two or more components.

4. The method according to claim 1, wherein step (ii) provides two blank fluid flows, and the blank fluid flows are brought into contact with, and provided either side of, the component fluid flow, thereby to generate three fluid flows.

5. The method according to claim 1, wherein step (iii) more particularly comprises bringing the flow (i) into contact with the flow (ii) in a channel, thereby to generate two laminar flows.

6. A method for analysing a change in the composition of a fluid comprising one or more components, the method comprising the step of taking a first sample from the fluid at a first time and performing a method according to claim 1, thereby to determine the composition of the fluid at the first time; and taking a second sample from the fluid at a second time, which is after the first time, and performing an analysis to determine the composition of the fluid at the second time.

7. A method for determining the concentration of a component in a composition, the method comprising performing a method according to claim 1, and determining the concentration of the component from a resolved diffusion profile of the composition.

8. A method for determining the diffusion coefficient of one or more components, the method comprising the steps of:
(i) providing a component fluid flow comprising one or more components;
(ii) providing a blank fluid flow;
(iii) flowing the component fluid flow and the blank fluid flow laminarly in a channel;
(iv) measuring lateral diffusion of the one or more components from the component flow into the blank fluid flow at a plurality of diffusion times; and
(v) comparing the measured lateral diffusion profiles of the one or more components from step (iv) with a series of distributions for components having known hydrodynamic radii, thereby determining a diffusion coefficient value for one of the one or more components from the lateral diffusion measurements of step (iv) and the hydrodynamic radius of each of the two or more components.

* * * * *